US006255476B1

(12) United States Patent
Vinayak et al.

(10) Patent No.: US 6,255,476 B1
(45) Date of Patent: Jul. 3, 2001

(54) METHODS AND COMPOSITIONS FOR SYNTHESIS OF LABELLED OLIGONUCLEOTIDES AND ANALOGS ON SOLID-SUPPORTS

(75) Inventors: Ravi S. Vinayak, Mountain View; Linda G. Lee, Palo Alto; Khairuzzaman B. Mullah, Union City; Barnett B. Rosenblum, San Jose, all of CA (US)

(73) Assignee: PE Corporation (NY), Foster City, CA (US)

( * ) Notice: Subject to any disclaimer, the term of this patent is extended or adjusted under 35 U.S.C. 154(b) by 0 days.

(21) Appl. No.: 09/256,340

(22) Filed: Feb. 22, 1999

(51) Int. Cl.[7] ............................. C12Q 1/68; C07H 19/00; C07H 21/00; C07H 21/02; C07H 21/04

(52) U.S. Cl. .................... 536/25.32; 536/22.1; 536/23.1; 536/24.1; 536/24.3; 536/26.31; 536/24.32; 536/24.33; 536/25.3; 435/6; 436/501

(58) Field of Search ................................. 536/22.1, 23.1, 536/24.1, 24.3, 24.31, 24.32, 24.33, 25.3, 25.32; 435/6; 436/501

(56) References Cited

U.S. PATENT DOCUMENTS

| 5,141,813 | 8/1992 | Nelson | 428/402 |
|---|---|---|---|
| 5,290,925 | * 3/1994 | Fino | 536/25.32 |
| 5,367,066 | 11/1994 | Urdea et al. | 536/24.3 |
| 5,552,471 | 9/1996 | Woo et al. | 524/494 |
| 5,583,236 | 12/1996 | Brush | 549/220 |
| 5,736,626 | 4/1998 | Mullah et al. | 536/25.3 |
| 5,908,926 | * 6/1999 | Pirrung et al. | 536/25.34 |

FOREIGN PATENT DOCUMENTS

| 0 323 152 | 7/1989 | (EP) . |
|---|---|---|
| 0 786 468 | 7/1997 | (EP) . |

OTHER PUBLICATIONS

B. Mullah et al., "Automated Synthesis of Double Dye–Labeled Oligonucleotides Using Tetramethylrhodamine (TAMRA) Solid Supports," *Tetrahedron Letters*, vol. 38, No. 33, 1997, pp. 5751–5754.
B. Mullah et al., "Efficient Synthesis of Double Dye–Labeled Oligodeoxyribonucleotide Probes and their Application in Real Time PCR Assay," *Nucleic Acids Research*, vol. 26, No. 4, Feb. 15, 1998, pp. 1026–1031.
Andrus, Alex, "Chemical methods for 5' non–isotopic labelling of PCR probes and primers," *A Practical Approach*, Oxford University Press, Ed. M. J. McPherson, Chapt. 3, pp. 39–54 (1995).
Dueholm et al., "Synthesis of Peptide Nucleic Acid Monomers Containing the Four Natural Nucleobases: Thymine, Cytosine, Adenine, and Guanine and Their Oligomerization," *J. Org. Chem.* 59:5767–5773 (Mar., 1994).
Hermanson, Greg T., "Modifications of Nucleic Acids and Oligonucleotides," *Bioconjugate Techniques*, Academic Press, pp. 40–55 (1996).

(List continued on next page.)

*Primary Examiner*—Jezia Riley
(74) *Attorney, Agent, or Firm*—Alex Andrus

(57) ABSTRACT

Methods and compositions to label oligonucleotides and analogs directly on a solid-support having the structure

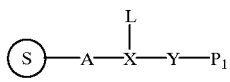

where S is a solid-support, A is a cleavable linker, X is a moiety with three or more attachment sites, L is a label, Y is a nucleophile, i.e. O, NH, NR or S, and $P_1$ is an acid cleavable protecting group are provided. The labelled solid-support is reacted in a cyclical fashion to synthesize a labelled oligonucleotide on a solid-support in the 5' to 3' direction, having the structure:

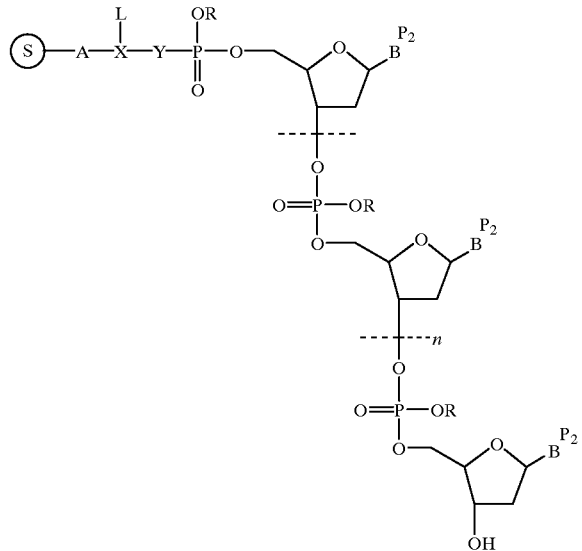

Labelled oligonucleotides are also synthesized by reacting: (i) a label reagent bearing functionality consisting of carboxylic acid, sulfonic acid, phosphonic acid, or phosphoric acid, (ii) an oligonucleotide on solid support with nucleophilic functionality, and (iii) a coupling reagent, whereby an ester, amide, thioester, sulfonamide, sulfonate, phosphonate, phosphoramidate, phosphorothioate, or phosphate bond is formed. The labelling reaction may be conducted at label sites including the 5' terminus, the 3' terminus, a nucleobase, an internucleotide linkage, a sugar, amino, sulfide, hydroxyl, and carboxyl.

34 Claims, 7 Drawing Sheets

OTHER PUBLICATIONS

Hermanson, Greg T., "Chemical Modification of Nucleic Acids and Oligonucleotides," *Bioconjugate Techniques*, Academic Press, pp. 643–671 (1996).

Keller et al., Labeling The 5'–Terminus of Amino–Linked Oligonucleotides With A Reporter Group On A Solid Support *DNA Probes Backgrounds Application Procedures*, Second Editions, Section 3, pp. 121–123 (1993).

Theisen et al., "Fluorescent dye phosphoramidite labelling of oligonucleotides," *Oxford University Press*, pp. 99–100 (1992).

Wagner et al., "An Inverse Approach In Oligodeoxyribonucleotide Synthesis," *Nucleosides & Nucleotides* 16(7–9): 1657–1660 (1997).

\* cited by examiner

FAM

TET

HEX

JOE

NED

VIC

TAMRA

ROX

DABCYL

DABSYL

NTB

```
                        SEQUENCE LISTING

<160> NUMBER OF SEQ ID NOS: 8

<210> SEQ ID NO 1
<211> LENGTH: 18
<212> TYPE: DNA
<213> ORGANISM: Unknown
<220> FEATURE:
<223> OTHER INFORMATION: Test Sequence

<400> SEQUENCE: 1
tgtaaaacga cggccagt                                                 18

<210> SEQ ID NO 2
<211> LENGTH: 18
<212> TYPE: DNA
<213> ORGANISM: Unknown
<220> FEATURE:
<223> OTHER INFORMATION: Test Sequence

<400> SEQUENCE: 2
tcacagtctg atctcgat                                                 18

<210> SEQ ID NO 3
<211> LENGTH: 18
<212> TYPE: DNA
<213> ORGANISM: Unknown
<220> FEATURE:
<223> OTHER INFORMATION: Test Sequence

<400> SEQUENCE: 3
tcacagtctg atctcgat                                                 18

<210> SEQ ID NO 4
<211> LENGTH: 26
<212> TYPE: DNA
<213> ORGANISM: Unknown
<220> FEATURE:
<223> OTHER INFORMATION: Test Sequence

<400> SEQUENCE: 4
atgccctccc ccatgccatc ctgcgt                                        26

<210> SEQ ID NO 5
<211> LENGTH: 26
<212> TYPE: DNA
<213> ORGANISM: Unknown
<220> FEATURE:
<223> OTHER INFORMATION: Test Sequence

<400> SEQUENCE: 5
atgccctccc ccatgccatc ctgcgt                                        26

<210> SEQ ID NO 6
<211> LENGTH: 8
<212> TYPE: DNA
<213> ORGANISM: Unknown
```

```
<220> FEATURE:
<223> OTHER INFORMATION: Test Sequence

<400> SEQUENCE: 6 tcctcctt                                                           8

<210> SEQ ID NO 7
<211> LENGTH: 8
<212> TYPE: DNA
<213> ORGANISM: Unknown
<220> FEATURE:
<223> OTHER INFORMATION: Test Sequence

<400> SEQUENCE: 7 tcctcctt                                                           8

<210> SEQ ID NO 8
<211> LENGTH: 19
<212> TYPE: DNA
<213> ORGANISM: Unknown
<220> FEATURE:
<223> OTHER INFORMATION: Test Sequence

<400> SEQUENCE: 8
cctgcaggcc cgtgcccgt                                              19
```

METHODS AND COMPOSITIONS FOR SYNTHESIS OF LABELLED OLIGONUCLEOTIDES AND ANALOGS ON SOLID-SUPPORTS

FIELD OF THE INVENTION

The invention relates generally to the field of nucleic acid chemistry, and particularly to methods and compositions for labelling oligonucleotides on solid-supports. Label reagents include hybridization-stabilizing moieties, fluorescent dyes, fluorescence quenchers, energy-transfer dye sets, chemiluminescent dyes, metallo porphyrins, amino acids, proteins, peptides, enzymes, and affinity ligands.

1. References

Andrus, A. "Chemical methods for 5' non-isotopic labelling of PCR probes and primers" (1995) in *PCR 2: A Practical Approach*, Oxford University Press, Oxford, pp. 39–54.

Andrus, A., McCollum, C. and Zon, G. "Automated system for polynucleotide synthesis and purification" U.S. Pat. No. 5,047,524, issued Sep. 10, 1991.

Andrus, A., McCollum, C. and Zon, G. "Automated system for polynucleotide synthesis and purification" U.S. Pat. No. 5,262,530, issued Nov. 16, 1993.

Beaucage, S. and Iyer, R. "Advances in the synthesis of oligonucleotides by the phosphoramidite approach", Tetrahedron 48:2223–2311(1992).

Bergot, B., Chakerian, V., Connell, C., Eadie, J., Fung, S., Hershey, N., Lee, L., Menchen, S. and Woo, S. "Spectrally resolvable rhodamine dyes for nucleic acid sequence determination", U.S. Pat. No. 5,366,860, issued Nov. 22, 1994.

Blackburn, G. and Gait, M. Eds. "DNA and RNA structure" in *Nucleic Acids in Chemistry and Biology*, $2^{nd}$ Edition, (1996) Oxford University Press, pp. 15–81.

Bronstein, I. and Voyta, J., "Methods of using chemiluminescent 1,2-dioxetanes" U.S. Pat. No. 4,931,223, issued Jun. 5, 1990.

Bronstein, K., Fortin, J., Stanley, P., Stewart, G. and Kricka, L. "Chemiluminescent and bioluminescent reporter gene assays", Anal. Biochemistry 219:169–81 (1994).

Cardullo, R., Agrawal, S., Flores, C., Zamecnik, P. and Wolf, D. "Detection of nucleic acid hybridization by non-radiative fluorescence resonance energy transfer", Proc. Natl. Acad. Sci. 85:8790–8794 (1988).

Caruthers, M. and Beaucage, S. "Phosphoramidite compounds and processes", U.S. Pat. No. 4,415,732, issued Nov. 15, 1983.

Caruthers, M. and Matteucci, M. "Process for preparing polynucleotides", U.S. Pat. No. 4,458,066, issued Jul. 3, 1984.

Clegg, R. "Fluorescence resonance energy transfer and nucleic acids", Meth. Enzymol. 211:353–388 (1992).

Dib, C. Faure, S., Fizames, C., Samson, D., Drouot, N., Vignal, A., Millasseau, P., Marc, S., Hazan, J., Seboun, E., Lathrop, M., Gyapay, G., Morissette, J., Weissenbach J. "A comprehensive genetic map of the human genome based on 5,264 microsatellites", Nature 380:6570:152–4 (1996).

Dueholm, K., Egholm, M., Behrens, C., Christensen, L., Hansen, H., Vulpius, T., Petersen, K., Berg, R., Nielsen, P. and Buchardt, O. "Synthesis of peptide nucleic acid monomers containing the four natural nucleobases: thymine, cytosine, adenine, and guanine and their oligomerization", J. Org. Chem. 59:5767–73 (1994).

Egholm, M., Buchardt, O., Christensen, L., Behrens, C., Freier, S., Driver, D., Berg, R. and Kim, S. "PNA hybridizes to complementary oligonucleotides obeying the Watson-Crick hydrogen bonding rules", Nature 365:566–68 (1993).

Englisch, U. and Gauss, D. "Chemically modified oligonucleotides as probes and inhibitors", Angew. Chem. Int. Ed. Engl. 30:613–29 (1991).

Flanagan, W., Wagner, R., Grant, D., Lin, K. and Matteucci, M. "Cellular penetration and antisense activity by a phenoxazine-substituted heptanucleotide", Nature Biotech. 17:48–52 (1999).

Fodor, S., Pirrung, M., Read, J., and Stryer, L. "Array of oligonucleotides on a solid substrate", U.S. Pat. No. 5,445,934, issued Aug. 29, 1995.

Gong, B. and Yan, Y. "New DNA minor-groove binding molecules with high sequence-selectivities and binding affinities", Biochem. and Biophys. Res. Comm. 240:557–60 (1997).

Grossman, P., Bloch, W., Brinson, E., Chang, C., Eggerding, F., Fung, S., Iovannisci, D., Woo, S. and Winn-Dean, E. "High-density multiplex detection of nucleic acid sequences: oligonucleotide ligation assay and sequence-coded separation", Nucl. Acids Res. 22:4527–4534 (1994).

Hermanson, G. in *Bioconjugate Techniques* (1996) Academic Press, San Diego, pp. 40–55, 643–671.

Ju, J., Kheterpal, I., Scherer, J., Ruan, C., Fuller, C., Glazer, A. and Mathies, R. "Design and Synthesis of fluorescence energy transfer dye-labeled primers and their application for DNA sequencing and analysis", Analytical Biochemistry 231:131–140 (1995).

Keller, G. and Manak, M. in *DNA Probes Second Edition* (1993), Stockton Press, New York, pp. 121–23.

Kricka, L. in *Nonisotopic DNA Probe Techniques* (1992), Academic Press, San Diego, pp. 3–28.

Kubista, M. and Svanvik, N. "Probe for analysis of nucleic acids", WO 97/45539, Intl. Publ. Date Dec. 4, 1997.

Kutyavin, I., Lukhtanov, E., Gamper, H. and Meyer, R. "Covalently linked oligonucleotide minor groove binder conjugates", WO 96/32496, Intl. Publ. Date Oct. 17, 1996.

Lee, L., Spurgeon, S., Rosenblum, B. "Energy transfer dyes with enhanced fluorescence", U.S. Pat. No. 5,800,996, issued Sep. 1, 1998.

Lee, L., Spurgeon, S., Heiner, C., Benson, S., Rosenblum, B., Menchen, S., Graham, R., Constantinescu, A., Upadhya, K and Cassel, M. "New energy transfer dyes for DNA sequencing", Nucl. Acids Res. 25:2816–22 (1997).

Livak, K., Flood, S., Marmaro, J., Giusti, W. and Deetz, K. "Oligonucleotides with fluorescent dyes at opposite ends provide a quenched probe system useful for detecting PCR product and nucleic acid hybridization", PCR Methods and Applications 4:357–362 (1995).

Livak, K., Flood, S. and Marmaro, J. "Method for Detecting Nucleic Acid Amplification Using Self-Quenching Fluorescence Probe", U.S. Pat. No. 5,538,848, issued Jul. 23, 1996.

Livak, K., Flood, S., Marmaro, J. and Mullah, K. "Self-quenching fluorescence probe", U.S. Pat. No. 5,723,591, issued Mar. 3, 1998.

Lukhtanov, E., Kutyavin, I., Gamper, H. and Meyer, R. "Oligodeoxyribonucleotides with conjugated dihydropyrroloindole oligopeptides: Preparation and hybridization properties", Bioconjugate Chem. 6:418–26 (1995).

Menchen, S., Lee, L., Connell, C., Hershey, N., Chakerian, V., Woo, S. and Fung, S. "4,7-Dichlorofluorescein dyes as molecular probes", U.S. Pat. No. 5,188,934, issued Feb. 23, 1993.

Meyer, R. "Incorporation of modified bases in oligonucleotides" in *Protocols for Oligonucleotide Conjugates*, Ed. S. Agrawal (1994) Humana Press, Totowa, N.J., pp. 73–92.

Mullah, B. and Andrus, A. "Automated synthesis of double dye-labeled oligonucleotides using tetramethylrhodamine (TAMRA) solid supports", Tetrahedron Letters 38: 5751–5754 (1997).

Mullah, B. and Andrus, A. "Solid support reagents for the direct synthesis of 3'-labeled polynucleotides", U.S. Pat. No. 5,736,626, issued Apr. 7, 1998.

Mullah, B., Livak, K., Andrus, A. and Kenney, P. "Efficient synthesis of double dye-labeled oligodeoxyribonucleotide probes and their application in a real time PCR assay", Nucl. Acids Res. 26:1026–1031 (1998).

Nelson, P., Kent, M. and Muthini, S. "Oligonucleotide labeling methods 3. Direct labeling of oligonucleotides employing a novel, non-nucleosidic, 2-aminobutyl-1,3-propanediol backbone", Nucl. Acids Res. 20:6253–59 (1992).

Nelson, P. "Multifunctional controlled pore glass reagent for solid phase oligonucleotide synthesis", U.S. Pat. No. 5,141,813, issued Aug. 25, 1992.

Nielsen, P., Egholm, M., Berg, R. and Bucbardt, O. "Sequence-selective recognition of DNA by strand displacement with a thymidine-substituted polyamide", Science 254:1497–1500 (1991).

Stanton, T., Schindele, D., Renzoni, G., Pepich, B., Anderson, N., Clagett, J. and Opheim, K. "Preparation and use of monomeric phthalocyanine reagents" WO 8804777, Intl. Publ. Date: Jun. 30, 1988.

Theisen, P., McCollum, C. and Andrus, A. "Fluorescent dye phosphoramidite labelling of oligonucleotides", in *Nucleic Acid Symposium Series* No. 27, Oxford University Press, Oxford, pp. 99–100 (1992).

Tyagi, S. and Kramer, F. "Molecular Beacons: Probes that fluoresce upon hybridization", Nature Biotechnology, 14:303–08 (1996).

Van der Laan, A., Brill, R., Kuimelis, R., Kuyl-Yeheskiely, E., van Boom, J., Andrus, A. and Vinayak, R. "A convenient automated solid-phase synthesis of PNA-(5')-DNA-(3')-PNA chimera", Tetrahedron Lett. 38:2249–52 (1997).

Vinayak, R., van der Laan, A., Brill, R., Otteson, K., Andrus, A., Kuyl-Yeheskiely, E. and van Boom, J. "Automated chemical synthesis of PNA-DNA chimera on a nucleic synthesizer", Nucleosides & Nucleotides 16:1653–56 (1997).

Wagner, T. and Pfleiderer, W. "An inverse approach in oligodeoxyribonucleotide synthesis", Nucleosides & Nucleotides 16:1657–60 (1997).

Woo, S., Menchen, S. and Fung, S. "Rhodamine phosphoramidite compounds", U.S. Pat. No. 5,231,191, issued Jul. 27, 1993.

Woo, S. and Fung, S. "Solid support reagents for the synthesis of 3'-nitrogen containing polynucleotides", U.S. Pat. No. 5,552,471, issued Sep. 3, 1996.

2. Background

Non-isotopically labelled oligonucleotides are essential components in many important molecular biology applications, such as PCR amplification, DNA sequencing, antisense transcriptional and translational control of gene expression, genetic analysis, and DNA probe-based diagnostic testing (Keller, 1993; Kricka, 1992). Fluorescence detection of fluorescent dye-labelled oligonucleotides is the basis for nucleic acid sequence detection assays such as Taqman™ (Livak, 1996), Molecular Beacons (Tyagi, 1996), genetic linkage mapping (Dib, 1996), and oligonucleotide-ligation assay (Grossman, 1994).

Two general methods for labeling synthetic oligonucleotides have been established. In a first method, referred to herein as the "two-step solution labelling method", a nucleophilic functionality, e.g. a primary aliphatic amine, is introduced at a labelling attachment site on an oligonucleotide, e.g. a 5' terminus. After automated, solid-support synthesis is complete, the oligonucleotide is cleaved from the support and all protecting groups are removed. The nucleophile-oligonucleotide is reacted with an excess of a label reagent containing an electrophilic moiety, e.g. isothiocyanate or activated ester, e.g. N-hydroxysuccinimide (NHS), under homogeneous solution conditions (Hermanson, 1996; Andrus, 1995).

In a second alternative method, referred to herein as the "direct labeling method", a label is directly incorporated into the oligonucleotide during or prior to synthesis (Mullah, 1998; Nelson, 1992). The direct labelling method is preferred because it (i) does not require a post-synthesis reaction step, thereby simplifying the synthesis of labelled polynucleotides; and (ii) avoids the problems associated with the low reaction yield (<60%) typically encountered with the two-step solution labelling method, namely: (a) purification of the labeled oligonucleotide from excess label; (b) purification of the labeled oligonucleotide from unlabeled oligonucleotide; (c) high costs due to the low product yield and laborious analytical and purification procedures, and; (d) irreversible capping of the nucleophilic functionality during synthesis.

Certain fluorescent dyes and other labels have been functionalized as phosphoramidite reagents for 5' labelling (Theisen, 1992). However, some labels, e.g., digoxigenin, rhodamine dyes, and cyanine dyes, are too unstable to survive the harsh conditions and reagents used in reagent preparation and oligonucleotide synthesis, cleavage and deprotection. Thus, whenever such labels are used in current solid phase synthesis protocols, they must be attached using the less preferred two-step solution labelling method.

Therefore it is desirable to provide methods and reagents to label oligonucleotides and analogs directly on a solid-support upon which they are synthesized, under conditions which are rapid, economical, and compatible with chemically-labile functionality.

SUMMARY

The present invention is directed toward novel methods and compositions for synthesis of labelled oligonucleotides on solid-supports.

In a first aspect, the invention comprises a method for synthesis of labelled oligonucleotides on a labelled solid-support having the structure

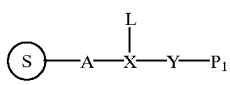

where S is a solid-support, A is a cleavable linker, X is a moiety with three or more attachment sites, L is a label, Y is a nucleophile, i.e. O, NH, NR or S, and $P_1$ is an acid cleavable protecting group. The labelled solid-support is reacted in a cyclical fashion with reagents to: (1) remove $P_1$ from Y, (2) couple Y with the 5' position of a 5'-phosphoramidite, 3' protected nucleoside, (3) cap any unreacted sites on the support, e.g. Y, if necessary, and (4) oxidize any phosphite linkages. The four steps are repeated until the entire labelled oligonucleotide is synthesized.

After synthesis is complete, protecting groups on the internucleotide phosphates and nucleobases of the labelled oligonucleotide may be removed by deprotection while the oligonucleotide remains on the solid-support. Alternatively, after synthesis is complete, the labelled oligonucleotide may be cleaved from the solid-support and then deprotected.

In a second aspect, the invention comprises a nucleoside bound to a solid-support having the structure

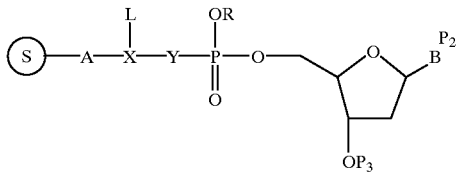

where S, A, X, L, and Y are defined as before, R is a phosphate protecting group or phosphotriester substituent; B is a nucleobase; $P_2$ is an exocyclic nitrogen protecting group; and $P_3$ is an acid-labile protecting group.

In a third aspect, the invention comprises an oligonucleotide bound to a solid-support having the structure

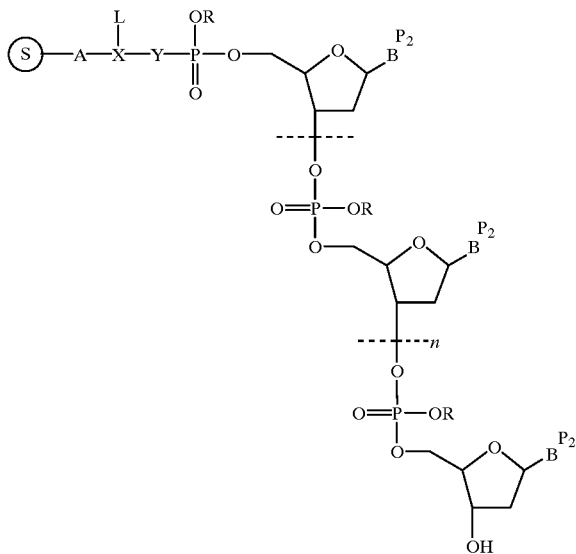

where the variable substituents are defined as before, and n is an integer preferably from about 0 to 100.

In a fourth aspect, the invention comprises a method for synthesizing a labelled a oligonucleotide by reacting: (i) a label reagent bearing functionality that can be converted into an electrophile, e.g. carboxylic acid, sulfoinic acid, phosphonic acid, or phosphoric acid, (ii) an oligonucleotide on a solid support with a nucleophilic functionality, e.g. alcohol, amine, or thiol, and (iii) a coupling reagent, whereby an ester, amide, thioester, sulfonamide, sulfonate, phosphonate, phosphoramidate, phosphorothioate, or phosphate bond is formed. The labelling method may be conducted on an oligonucleotide at label sites including the 5' terminus, the 3' terminus, a nucleobase, an internucleotide linkage, a sugar, amino, sulfide, hydroxyl, and carboxyl. The labelling reaction may be conducted on an oligonucleotide comprising one or more DNA, RNA, PNA and nucleic acid analog monomer units. The nucleic acid analogs may be nucleobase, sugar, and/or internucleotide analogs.

The labelled oligonucleotide may be synthesized either in the 5' to 3' direction, or in the 3' to 5' direction.

DETAILED DESCRIPTION OF THE PREFERRED EMBODIMENTS

Figure 1:
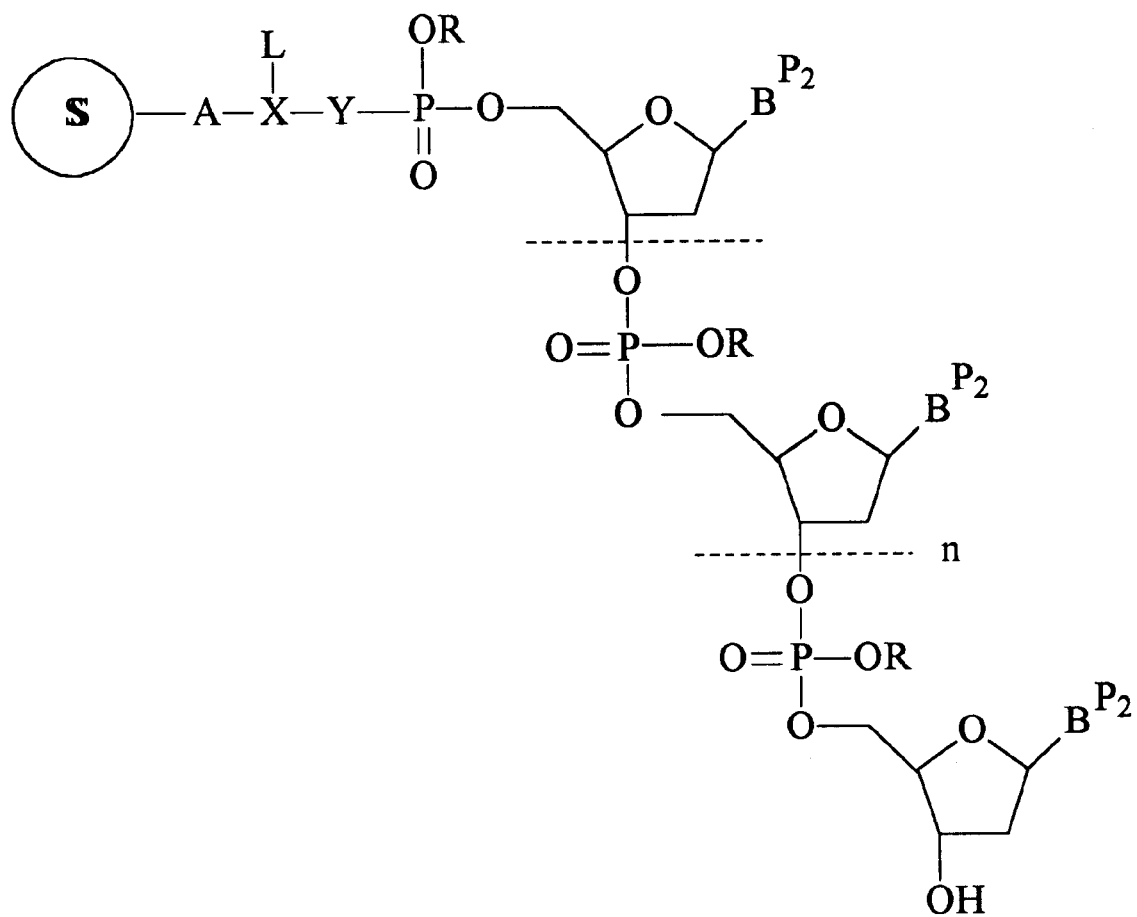
FIG. 1 Oligonucleotide attached to labelled-support at 5' terminus

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. Definitions

Unless stated otherwise, the following terms and phrases as used herein are intended to have the following meanings:

The terms "nucleic acid", "polynucleotide" or "oligonucleotide" mean polymers of nucleotide monomers or analogs thereof, including double and single stranded deoxyribonucleotides, ribonucleotides, α-anomeric forms thereof and the like. The oligonucleotide may comprise one or more DNA, RNA, and nucleic acid analog monomer units. The monomers are linked by internucleotide linkages, including phosphodiester bonds or phosphate analogs thereof, and associated counterions, e.g., $H^+$, $NH_4^+$, $Na^+$. Oligonucleotides typically range in size from a few monomeric units, e.g. 5–40, to several thousands of monomeric units. Whenever an oligonucleotide is represented by a sequence of letters, such as "ATGCCTG, " it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Nucleoside" refers to a compound consisting of a purine, deazapurine, or pyrimidine nucleobase, e.g., adenine, guanine, cytosine, uracil, thymine, deazaadenine, deazaguanosine, and the like, linked to a pentose at the 1'-position. When the nucleoside base is purine or 7-deazapurine, the pentose is attached to the nucleobase at the 9'-position of the purine or deazapurine, and when the nucleobase is pyrimidine, the pentose is attached to the nucleobase at the 1-position of the pyrimidine.

"Nucleotide" refers to a phosphate ester of a nucleoside, e.g., a triphosphate ester, wherein the most common site of esterification is the hydroxyl group attached to the C-5 position of the pentose.

The term "Watson/Crick base-pairing" refers to a pattern of specific pairs of nucleotides, and analogs thereof, that bind together through sequence-specific hydrogen-bonds, e.g. A pairs with T and U, and G pairs with C.

The term "analog" refers to analogs of nucleic acids made from monomeric nucleotide analog units, and possessing some of the qualities and properties associated with nucleic acids. Nucleic acid analogs may have modified nucleobase moieties, modified sugar moieties, and/or modified internucleotide linkages (Englisch, 1991). A preferred class of nucleic acid analogs in which the sugar and internucleotide moieties have been replaced with an 2-aminoethylglycine amide backbone polymer is peptide nucleic acids PNA (Nielsen, 1991).

"Attachment site" refers to a site to which a linker is attached.

"Linker" refers to one or more atoms comprising a chain connecting an oligonucleotide to a label or a solid-support.

"Chimera" as used herein refers to an oligonucleotide including one or more nucleotide and one or more nucleotide analog units.

"Lower alkyl", "lower alkylene" and "lower substituted alkylene" refers to straight-chain, branched, or cyclic groups consisting of 1–12 carbon atoms.

"Label" refers to a moiety covalently attached to an oligonucleotide. A preferred class of labels provides a signal for detection, e.g. fluorescence, chemiluminescence, and electrochemical luminescence (Kricka, 1992). Another preferred class of labels serve to enhance, stabilize, or influence hybridization, e.g. intercalators, minor-groove binders, and cross-linking functional groups (Blackburn, 1996). Detection labels include, but are not limited to, fluorescent dyes, such as fluorescein and rhodamine derivatives, cyanine dyes (Kubista, 1997), chemiluminescent dyes (Bronstein, 1990; Bronstein, 1994) and energy-transfer dyes (Clegg, 1992; Cardullo, 1988). Yet another preferred class of labels serve to effect the separation or immobilization of a molecule by specific or non-specific capture means (Andrus, 1995).

"Detection" refers to detecting, observing, or measuring an oligonucleotide on the basis of the properties of a label.

"Coupling reagents" include any reagent, activator, or additive that can form an ester, amide, thioester, sulfonamide, sulfonate, phosphonate, phosphoramidate, phosphorothioate, or phosphate bond between the nucleophile oligonucleotide on solid-support and the label.

II. Labelled-supports

In one aspect of the present invention comprises supports for the synthesis of labelled oligonucleotides. The labelled supports according to this aspect of the present invention have the structure:

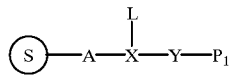

where S refers generally to a solid-support material useful for oligonucleotide synthesis, A is a cleavable linker, X is a moiety with three or more attachment sites, L is a label, Y is a nucleophile, i.e. O, NH, NR or S, and $P_1$ is an acid cleavable protecting group.

The solid-supports provide an insoluble media for sequential attachment of monomer units. A significant advantage of heterogeneous synthesis methods is that excess reagents in the liquid phase may be easily removed by filtration, thereby eliminating the need for purification steps between each reaction or each cycle. The characteristics of the solid-support, such as pore size, cross-link content, swelling, particle size, and surface area, should be optimized to allow for efficient diffusion of reagents in order to give rapid kinetics and high-yield reactions. Preferred support materials include high cross-link, non-swelling polystyrene (Andrus, 1993), controlled-pore-glass (Caruthers, 1984), silica, silica gel, polyacrylamide, magnetic beads (Stamm, 1995), polyacrylate, hydroxyethylmethacrylate, polyamide, polyethylene, polyethyleneoxy, and copolymers or grafts of such. Physical configurations of solid-supports include small particles, beads, membranes, frits, non-porous surfaces, slides, plates, micromachined chips, alkanethiol-gold layers, addressable arrays, vectors, plasmids, or polynucleotide-immobilizing media (Fodor, 1995). In some embodiments, it may be desirable to create an array of physically separate synthesis regions on the support with, for example, wells, raised regions, dimples, pins, trenches, rods, inner or outer walls of cylinders, and the like.

The cleavable linker A may be comprised of any functionality such as: (i) esters and other base-labile linkers that are cleaved by basic reagents, (ii) silyl ethers that are cleaved by nucleophiles such as fluoride, or (iii) disulfide groups and other groups that are cleaved under oxidation/reduction conditions with reagents such as dithiothreitol (DTT). The bonds that are cleaved in above examples of linkers A are shown by the arrows below:

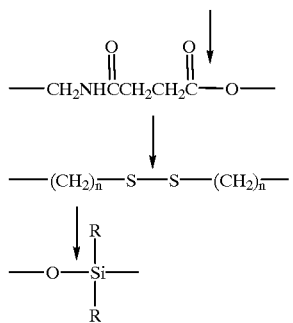

The moiety X may be any group comprised of attachment sites for attachment of the solid-support through linker A, a label L, and the oligonucleotide.

Labels L are any group or moiety covalently attached to the oligonucleotide. Labels may be comprised of hybridization-stabilizing moieties, (e.g. minor-groove binders, intercalators, and cross-linking agents), fluorescent dyes, fluorescence quenchers, energy-transfer dye sets, chemiluminescent dyes, amino acids, proteins, peptides, enzymes, and affinity ligands.

Y is a group nucleophilic relative to carbon, e.g. O, NH, NR, and S and attaches X to the oligonucleotide. Y has an acid-cleavable protecting group, $P_1$, which may be DMT, MMT, trityl, substituted trityl, pixyl, or trialkylsilyl. The protecting group $P_1$ is removed to commence oligonucleotide synthesis from the nucleophile Y.

III. Synthesis of Labelled-supports

The solid-supports S are derivatized with reactive functionality to which is attached a linker unit, A-X-Y. Preferably the reactive functionality is a primary amino group with a preferable loading of 5–100 $NH_2$ per gram. A linker unit, or spacer, A-X-Y, is then covalently attached to the reactive functionality of the solid-support. A second attachment site on A-X-Y attaches to labels. A third attachment site on A-X-Y allows synthesis of the oligonucleotide chain. Typically A contains an ester group which is cleavable under basic conditions, e.g. ammonium hydroxide, to allow separation of the solid-support from the oligonucleotide and any labels attached to the oligonucleotide.

The linker unit A-X-Y may be attached to the solid-support as: (i) one unit with a label L, or (ii) as a unit without a label L, where the label L is then attached to the linker X by the reactions:

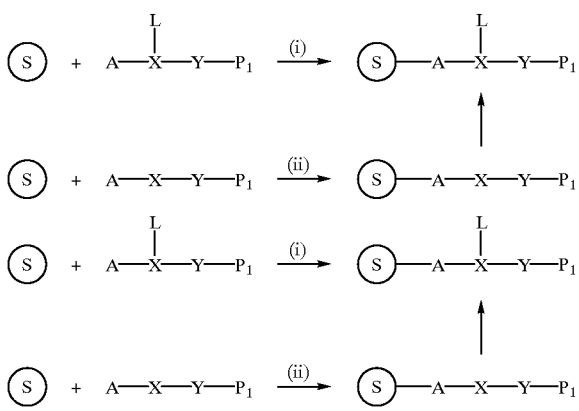

Figure 2:
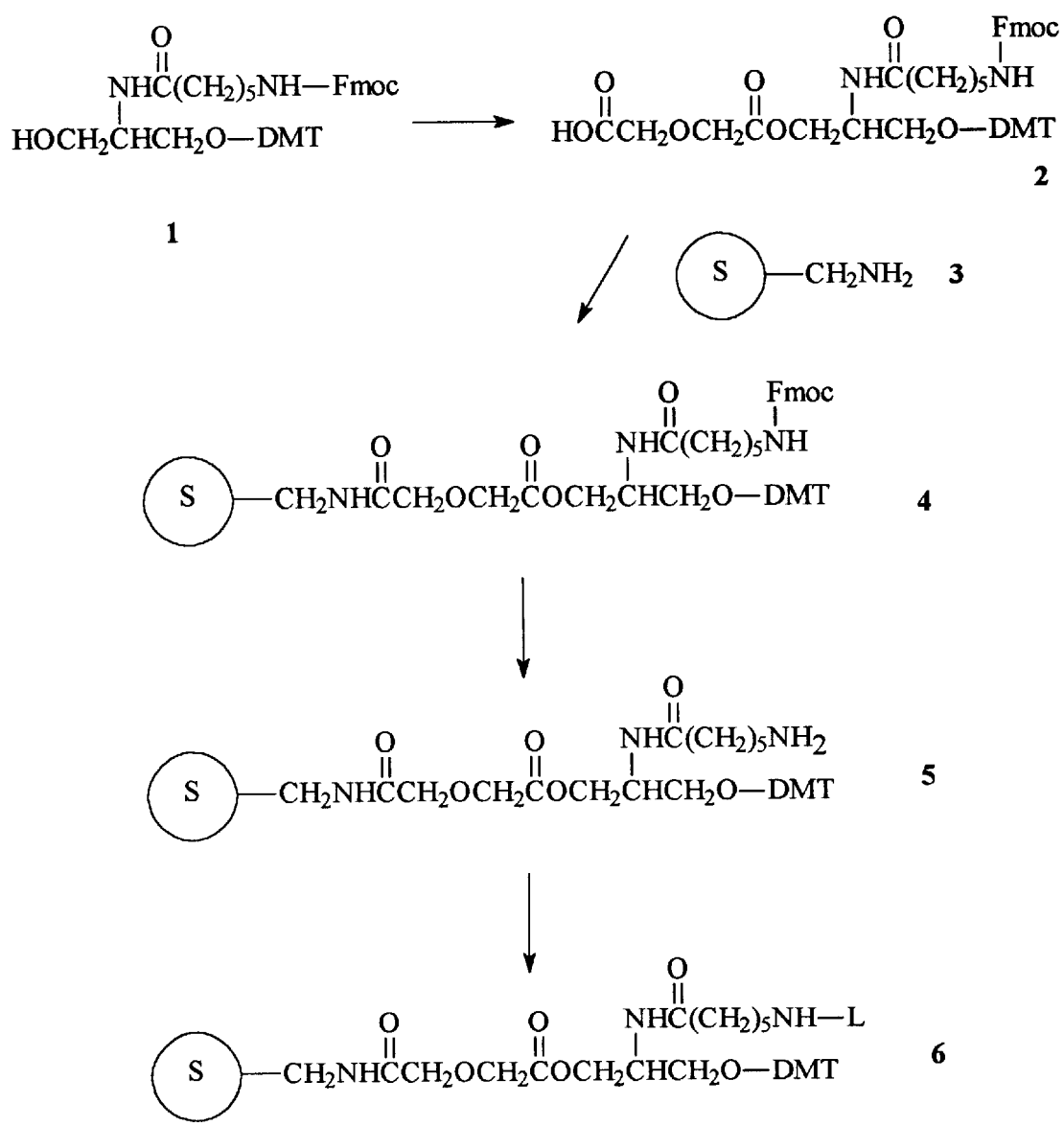
FIG. 2 Synthetic route to support-linker-label reagents 1 to 6

FIG. 2 shows the exemplary route to a labelled-support (ii) where the linker 1 (X-Y-P$_1$) is converted to 2 (A-X-Y-P$_1$) and attached to aminomethyl, highly-cross linked polystyrene 3. The resulting product 4 is deprotected to 5. A pre-activated label, e.g. TAMRA-NHS (N-hydroxysuccinimide ester of 5-carboxy tetramethylrhodamine) is covalently attached to 5 to yield the labelled-support 6, ready for oligonucleotide synthesis.

A preferred group of labelled solid-supports is embodied in the structure 6 (FIG. 2 and below)

6

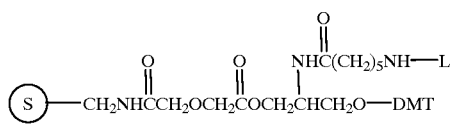

where S is high cross-link polystyrene or controlled-pore glass,
A is

X is

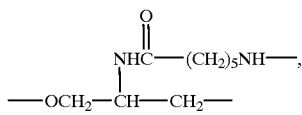

L is minor-groove binder, cyanines, fluorescent dyes, or energy-transfer dye sets, Y is oxygen, and P$_1$ is DMT.

The asymmetric carbon in X of 6 leads to diastereomer isomers of labelled oligonucleotides. These particular isomers have the advantage of not resolving into separate peaks during analysis by HPLC or capillary electrophoresis. Other diastereomeric linkers for attaching labels to oligonucleotides may show diastereomeric resolution, exemplified by double peaks in analysis (Mullah, 1998; Woo, 1996). Where labelled oligonucleotides prepared from 6 are used in primer extension experiments such as DNA sequencing (Lee, 1997), DNA fragment analysis (Grossman, 1994) and PCR (Livak, 1996), the fragments and amplification products are similarly advantaged by not separating into diastereomeric populations which can hinder data analysis.

IV. Synthesis of Labelled Oligonucleotides on Labelled-support in the 5' to 3' Direction Generally, the methods and compositions of the present invention utilize the phosphoramidite synthesis method, preferred because of its efficient and rapid coupling and the stability of the starting nucleoside monomers (Caruthers, 1983; Beaucage, 1983; Beaucage, 1992). The phosphoramidite method entails cyclical addition of nucleotide monomer units to an oligonucleotide chain growing on a solid-support, most commonly in the 3' to 5' direction in which the 3' terminus nucleoside is attached to the solid-support at the beginning of synthesis. The method is usually practiced using automated, commercially available synthesizers (PE Biosystems, Caruthers, 1984). The 5' to 3' direction embodiment of the present invention cyclically adds a 5'-phosphoramidite, 3' protected nucleoside monomer (Wagner, 1997) having the structure 7:

7

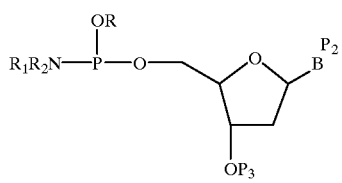

where, R is a protecting group or substituent, e.g. cyanoethyl, methyl, lower alkyl, substituted alkyl, phenyl, aryl, and substituted aryl; R$_1$ and R$_2$ are amine substituents, e.g. isopropyl, morpholino, methyl, ethyl, lower alkyl, cycloalkyl, and aryl; P$_2$ is an exocyclic nitrogen protecting group such as benzoyl, isobutyryl, acetyl, phenoxyacetyl, aryloxyacetyl, dimethylformamidine, dialkylformamidine, and dialkylacetamidine; and P$_3$ is an acid-labile protecting group such as DMT, MMT, pixyl, trityl, and trialkylsilyl.

An oligonucleotide is synthesized with the 5' terminus attached to the solid-support and a free, unattached 3' terminus (FIG. 1).

The following briefly describes the steps of a synthesis cycle, in the present invention, using the phosphoramidite method. First, a solid support, e.g. 6, is treated with a protic acid, e.g., trichloroacetic acid or dichloroacetic acid, to remove an acid labile protecting group, e.g., DMT, freeing a nucleophile, e.g. hydroxyl, for a subsequent coupling reaction. An activated intermediate is then formed by simultaneously adding a 5'-phosphoramidite, 3' protected nucleoside monomer 7 and a weak acid, e.g. tetrazole or the like, to the reaction vessel on the synthesizer, i.e. synthesis column. Nucleoside addition is typically complete within 30 to 300 s, preferably about 90 s. Next, a capping step may be performed which terminates any oligonucleotide chains that did not undergo nucleoside addition by acylation of the 3' hydroxyl. Capping is preferably done with acetic anhydride and 1-methylimidazole, but other acylating agents may be used. The internucleotide linkage is then converted from the phosphite to the more stable phosphotriester by oxidation using iodine as the preferred oxidizing agent and water as the oxygen donor to give the structure:

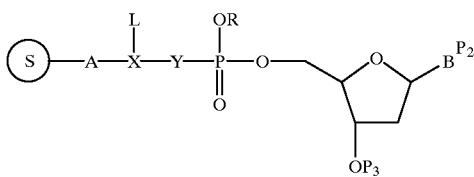

Alternatively, the internucleotide phosphite can be oxidized to an internucleotide analog such as phosphorothioate or phosphoramidate. After oxidation, the next 3' hydroxyl protecting group, e.g. DMT, is removed with the protic acid, e.g., trichloroacetic acid or dichloroacetic acid, and the cycle is repeated until chain elongation is complete (FIG. 1).

V. Post-Synthesis Labelling of Oligonucleotides on Solid-support

Labels may be attached at various attachment sites on oligonucleotides and nucleic acid analogs, including: (i) a terminus, e.g. 5' and/or 3' termini of probes, (ii) an internucleotide linkage, (iii) a sugar, or (iv) a nucleobase. Labels are most conveniently and efficiently introduced at the 5' terminus, the labelling site which least destabilizes hybridization and least interferes with 3' primer-extension reactions (Kricka, 1992; Hermanson, 1996). A preferred 5' linker reagent is a protected-amino, phosphoramidite with the structure 8:

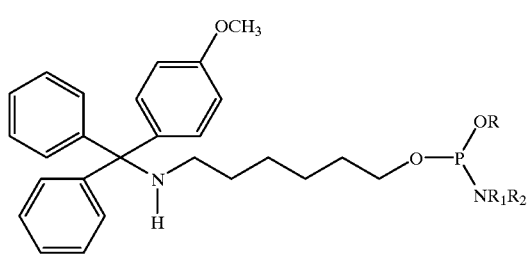

where R is an oxygen protecting group or substituent, e.g. cyanoethyl, methyl, lower alkyl substituted alkyl, phenyl, aryl, or substituted aryl; and $R_1$ and $R_2$ are amino substituents, e.g. isopropyl, morpholino, methyl, ethyl, lower alkyl, cycloalkyl, or aryl. Coupling of the above reagent with a 5'-hydroxyl group of a support-bound oligonucleotide and a weak acid activator, e.g. tetrazole, yields the monomethoxytrityl (MMT) protected oligonucleotide. After phosphite oxidation, the MMT group can be removed from the amine group with the same acid reagent, e.g. TCA or DCA, to unveil the reactive primary amine nucleophile for coupling with a label reagent. The hexyl linker can easily be replaced by other inert linkers of shorter, e.g. ethyl, or longer length, e.g. dodecyl, also including aryl groups and other functionality. Alternatively, thiol or hydroxyl nucleophiles can be introduced at the 5' terminus or other sites on an oligonucleotide bound to a solid-support. Preferred thiol-protected phosphoramidite reagents are 9 and 10:

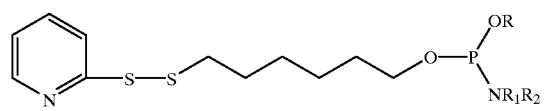

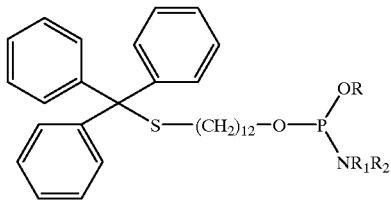

Such reagents may be similarly coupled to the 5' hydroxyl group, phosphite oxidized, and thiol protecting group removed to give a reactive thiol nucleophile. Resulting 5'-linked nucleophile-oligonucleotides bound to a solid-support may be represented as:

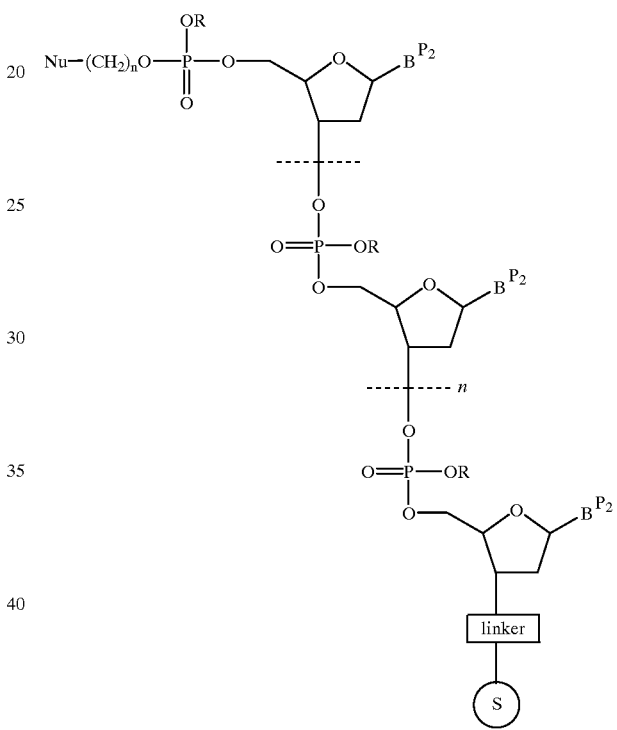

Nu = HO, HNR, H$_2$N, HS
$n$ = 2–12 linker = —A—X—Y—
            | L

The labelling reaction is conducted between: (i) an oligonucleotide bound to a solid-support where the oligonucleotide has reactive nucleophilic functionality, e.g. HO, HNR, H$_2$N, or HS, (ii) a label with CO$_2$H (carboxyl), SO$_3$H (sulfonate), RPO$_3$H (phosphonate), or OPO$_3$H (phosphate) functionality, (iii) a coupling reagent, and (iv) a solvent or mixture of solvents. The reaction may be conducted at a temperature between 0–100° C. and preferably at ambient temperature of about 20° C.

Preferred coupling reagents include HATU (O-(7-azabenzotriazol-1-yl)-N,N,N',N'-tetramethyluronium hexafluorophosphate), HBTU (O-benzotriazol-1-yl)-N,N,N',N'-tetramethyluronium hexafluorophosphate), TBTU (2-(1H-benzotriazo-1-yl)-1-1,3,3-tetramethyluronium hexafluorophosphate), TFFH (N,N',N'',N'''-tetramethyluronium 2-fluoro-hexafluorophosphate), BOP (benzotriazol-1-yloxytris(dimethylamino)phosphonium hexafluorophosphate), PyBOP (benzotriazole-1-yl-oxy-trispyrrolidino-phosphonium hexafluorophosphate, EEDQ (2-ethoxy-1-etboxycarbonyl- 1,2-dihydro-quinoline), DCC (dicyclohexylcarbodiimide); DIPCDI (diisopropylcarbodiimide), HOBt (1-hydroxybenzotriazole), N-hydroxysuccinimide, MSNT (1-(mesitylene-2-sulfonyl)-3-nitro-1H-1,2,4-triazole, and aryl sulfonyl halides, e.g. tri-isopropylbenzenesulfonyl chloride.

Figure 7:
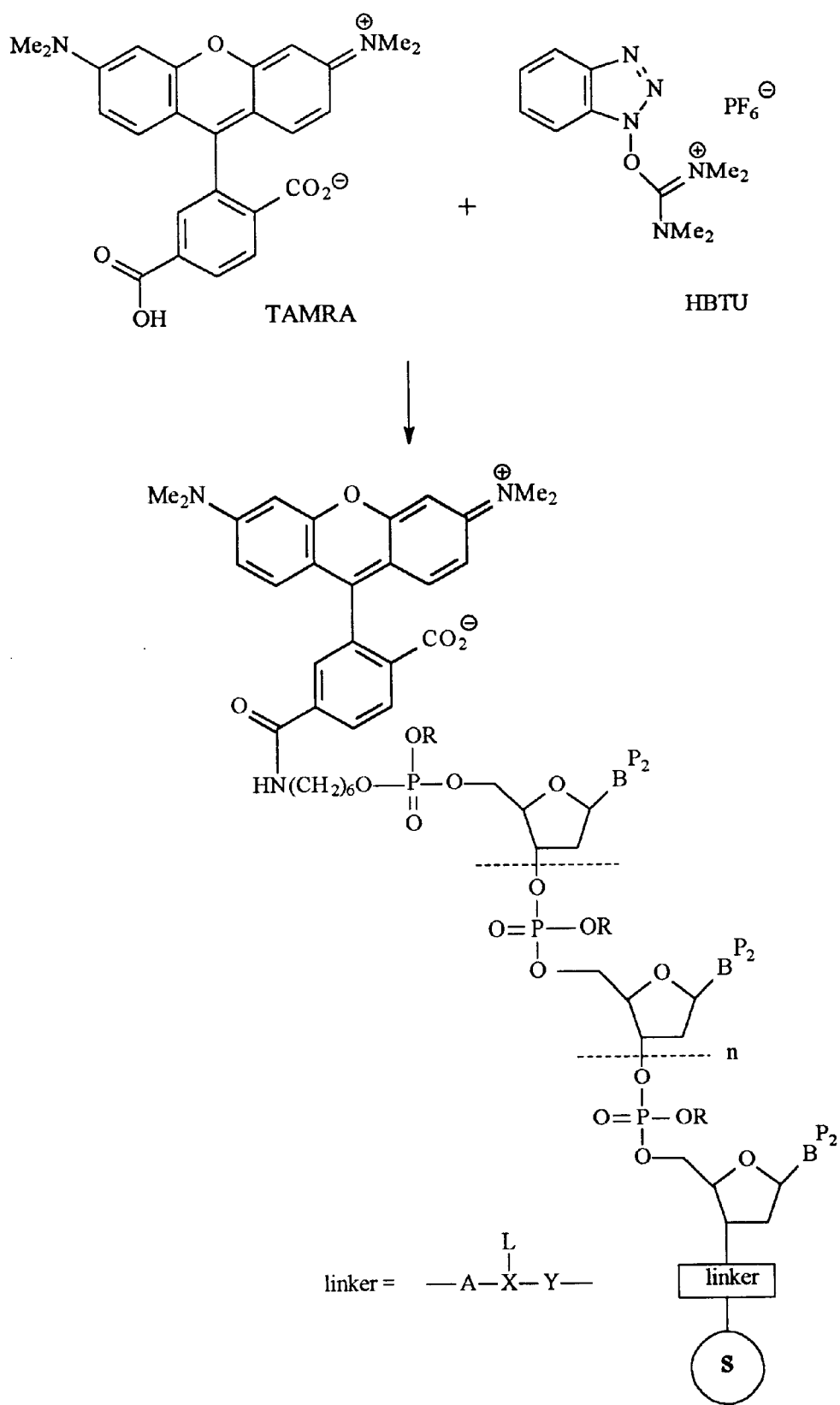
FIG. 7 Coupling of TAMRA labelling reagent with HBTU coupling reagent to 5' aminohexyl oligonucleotide on solid-support.

Prior or separate activation ("pre-activation") of a label functionality is thereby not necessary to the practice of the present invention. For example, the present invention does not require prior conversion of a carboxyl group to an NHS ester for reaction with a nucleophile-oligonucleotide (FIG. 7).

VI. Labels

A label L may be any moiety covalently attached to an oligonucleotide or nucleic acid analog.

A preferred class of labels are detection labels, which may provide a signal for detection of the labelled oligonucleotide by fluorescence, chemiluminescence, and electrochemical luminescence (Kricka, 1992). Fluorescent dyes useful for labelling oligonucleotides include fluoresceins (Menchen, 1993), rhodamines (Bergot, 1994), cyanines (Kubista, 1997), and metal porphyrin complexes (Stanton, 1988).

Figure 3:
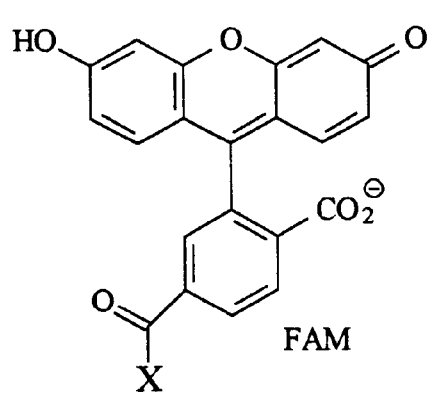
FIG. 3 Fluorescent dye labels: FAM, TET, HEX, JOE, NED, VIC
Figure 3:
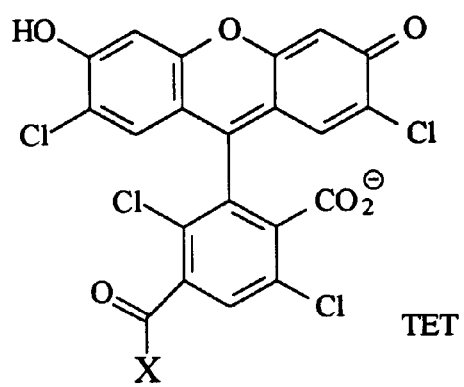
Figure 3:
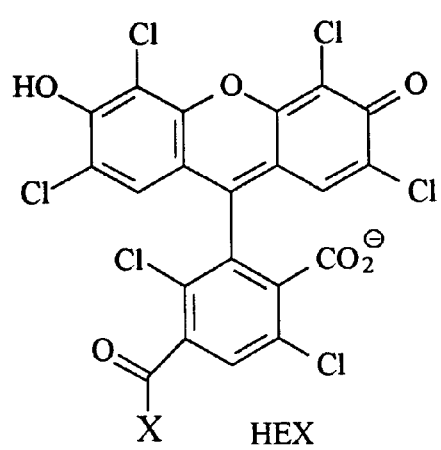
Figure 3:
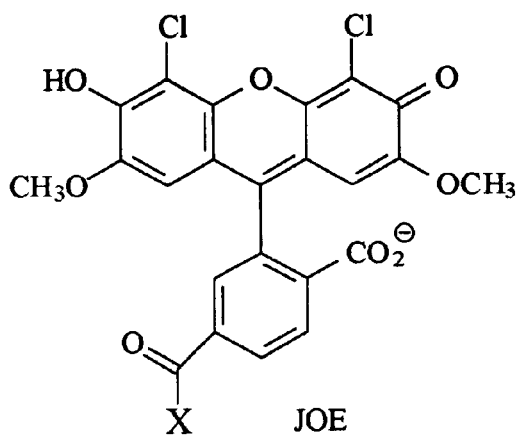
Figure 3:
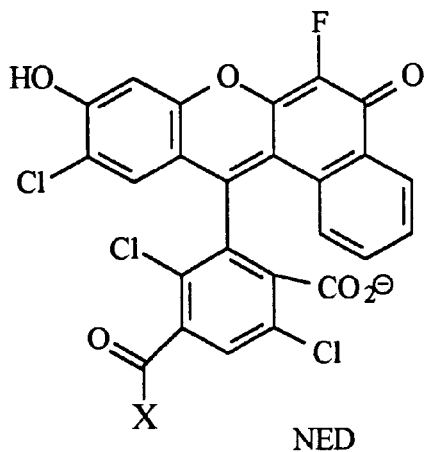
Figure 3:
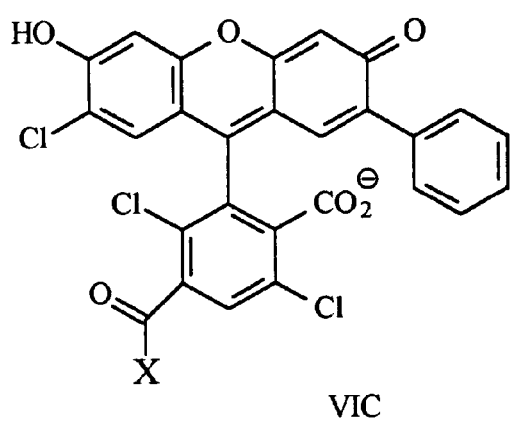
Figure 4:
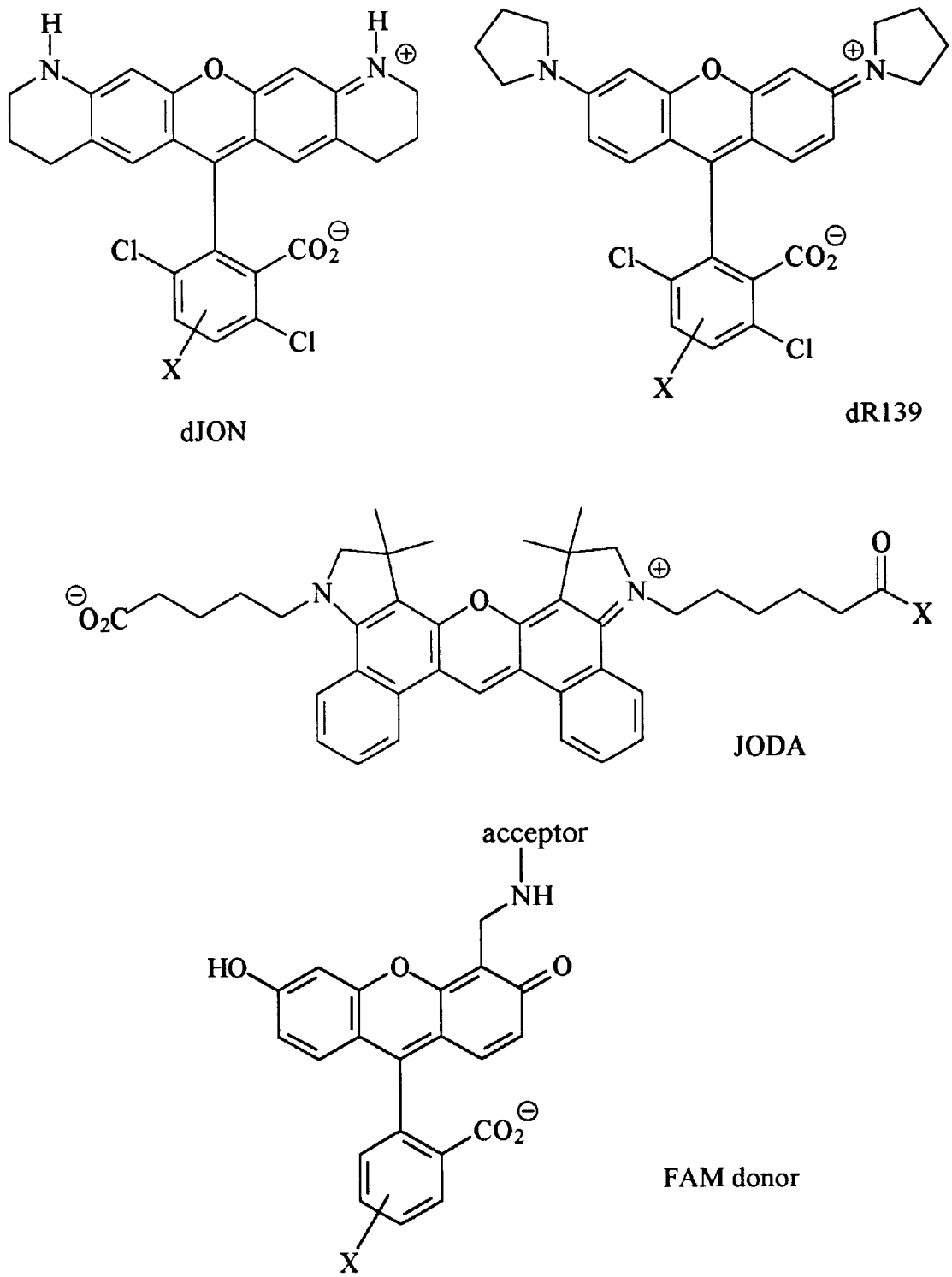
FIG. 4 Fluorescent dye labels: dJON, dR139, JODA and energy-transfer donor FAM

Examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), 2'-chloro-7'-phenyl-1,4-dichloro-6-carboxyfluorescein (VIC), and (JODA) (FIGS. 3 and 4). The 5-carboxyl, and other regio-isomers, may also have useful detection properties. Fluorescein and rhodamine dyes with 1,4-dichloro substituents are especially preferred.

Another preferred class of labels include quencher moieties. The emission spectra of a quencher moiety overlaps with a proximal intramolecular or intermolecular fluorescent dye such that the fluorescence of the fluorescent dye is substantially diminished, or quenched, by fluorescence resonance energy transfer (FRET). Oligonucleotides which are intramolecularly labelled with both fluorescent dye and quencher moieties are useful in nucleic acid hybridization assays, e.g. the "Taqman™" exonuclease-cleavage PCR assay (Livak, 1998; Livak, 1996).

Figure 5:
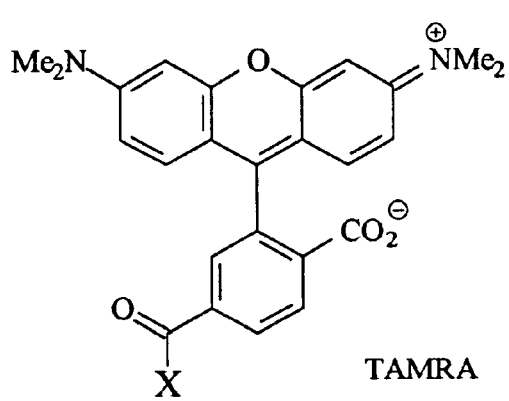
FIG. 5 Fluorescence quencher labels: TAMRA, ROX, DABCYL, DABSYL, NTB
Figure 5:
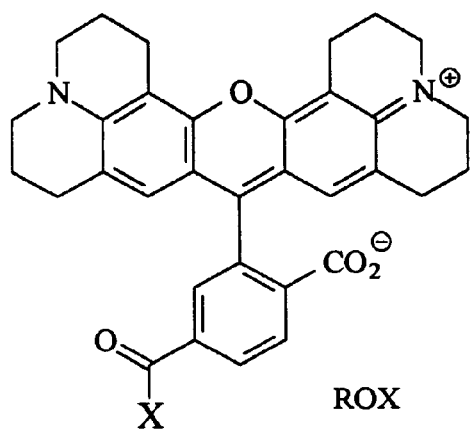
Figure 5:
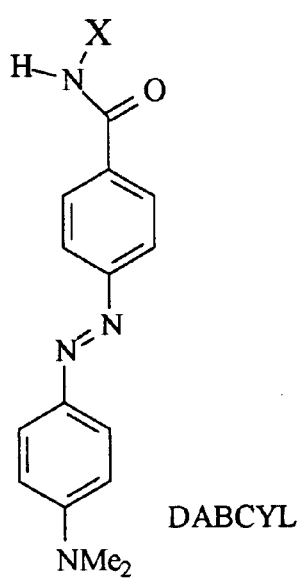
Figure 5:
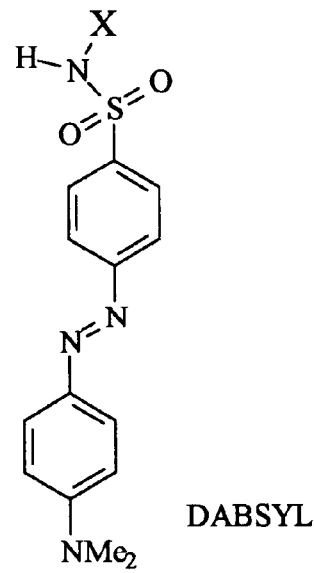
Figure 5:
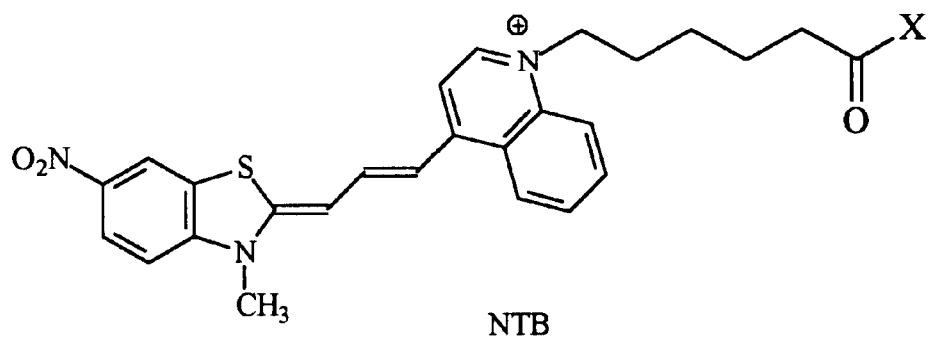

Particularly preferred quenchers include but are not limited to (i) rhodamine dyes selected from the group consisting of tetramethyl-6-carboxyrhodamine (TAMRA), tetrapropano-6-carboxyrhodamine (ROX), and (ii) DABSYL, DABCYL, cyanine dyes including nitrothiazole blue (NTB), anthraquinone, malachite green, nitrothiazole, and nitroimidazole compounds and the like (FIG. 5).

Fluorescein (left) and rhodamine (right) derivatives of the present invention may bear the general structure and numbering system below, where X is a linker, and may be substituted at one or more of the numbered positions.

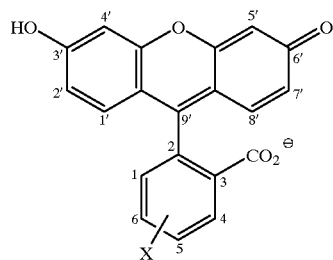

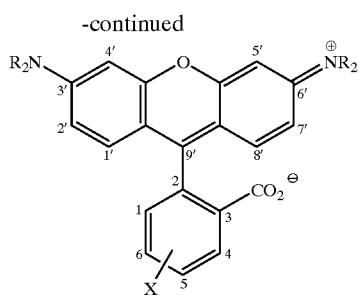

Cyanine labels may have the structure

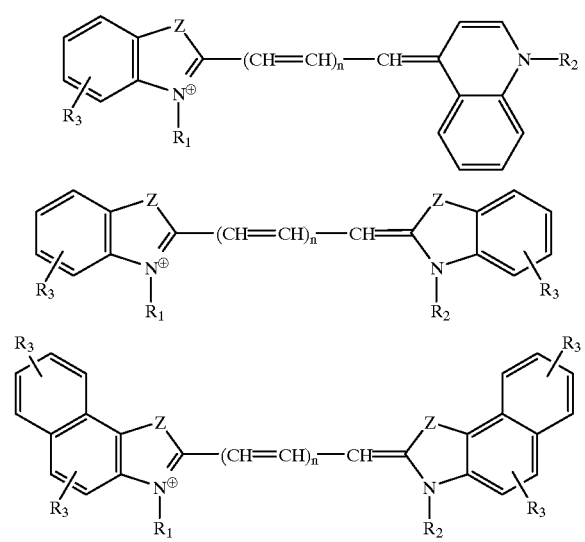

where $R_1$ or $R_2$ is H, lower alkyl, lower alkylene, lower substituted alkylene, phenyl, or aryl; Z is $CR_1R_2$, S, O, NH, or $N-R_1$; $R_3$ is nitro, halo, sulfonate, hydroxy, amino, lower alkyl, or trihalomethyl, and n=0–2 (Kubista, 1997). The attachment site X for labelling of oligonucleotides may be at $R_1$, $R_2$, or $R_3$.

Energy-transfer dyes are a preferred class of oligonucleotide labels. An energy-transfer dye label includes a donor dye linked to an acceptor dye (Lee, 1998). Light, e.g. from a laser, at a first wavelength is absorbed by a donor dye, e.g. FAM. The donor dye emits excitation energy absorbed by the acceptor dye. The acceptor dye fluoresces at a second wavelength, with an emission maximum about 100 nm greater than the absorbance maximum of the donor dye.

The donor dye and acceptor dye moieties of an energy-transfer label may be attached by a linker such as

linking the 4' or 5' positions of the donor dye, e.g. FAM, and a 5- or 6-carboxyl group of the acceptor dye.

Metal porphyrin complexes are also a preferred class of oligonucleotide labels (Stanton, 1988). One example is aluminum phthalocyanine tetrasulfonate, structure shown below:

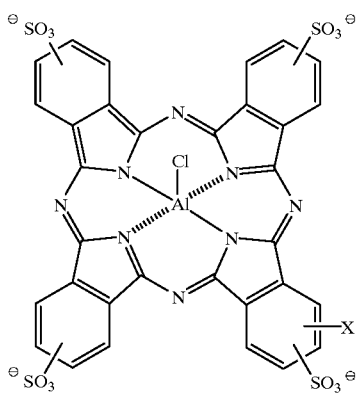

Another preferred class of labels comprise chemiluminescent compounds. Particularly preferred are 1,2-dioxetane chemiluminescent moieties (Bronstein, 1994; Bronstein, 1990) having the structure

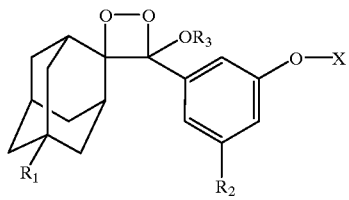

where $R_1$ is hydrogen or halogen; $R_2$ is phosphate, galactoside, glucoside, glucuronide, trialkylsilyloxy, acyloxy, or hydrogen; $R_3$ is methyl, ethyl, and lower alkyl, and X is a linker to an oligonucleotide. Affinity ligands include biotin, 2,4-dinitrophenyl, digoxigenin, cholesterol, polyethyleneoxy, and peptides.

Figure 6:
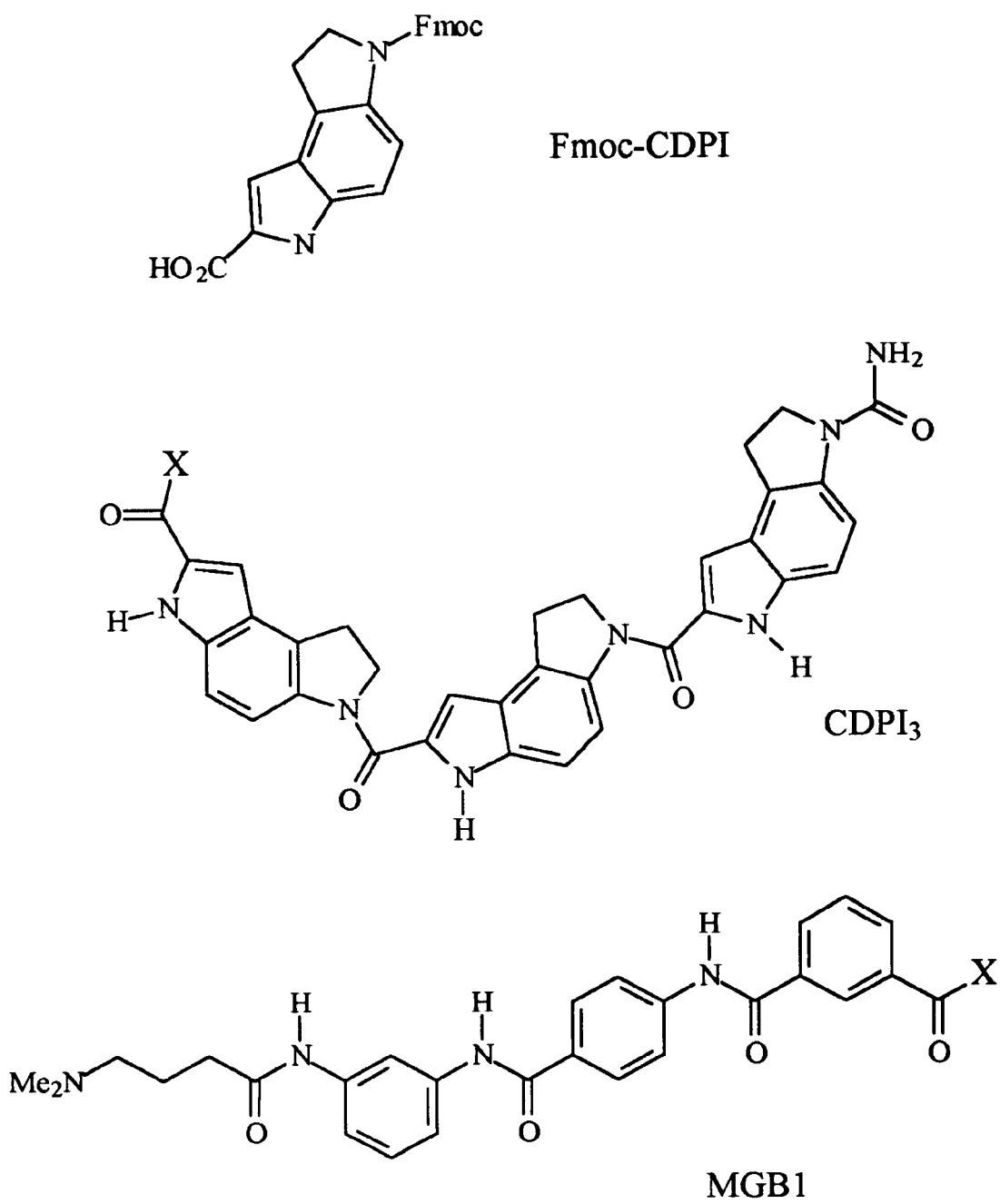
FIG. 6 Minor groove binder labels: MGB1, CDPI monomer, $CDPI_3$

Another preferred class of labels, referred to herein as hybridization-stabilizing moieties, include but are not limited to minor groove binders, intercalators, polycations, such as poly-lysine and spermine, and cross-linking functional groups. Hybridization-stabilizing moieties may increase the stability of base-pairing, i.e. affinity, or the rate of hybridization, exemplified by high thermal melting temperatures, $T_m$, of the duplex. Hybridization-stabilizing moieties serve to increase the specificity of base-pairing, exemplified by large differences in $T_m$ between perfectly complementary oligonucleotide and target sequences and where the resulting duplex contains one or more mismatches of Watson/Crick base-pairing (Blackburn, 1996). Preferred minor groove binders include Hoechst 33258, $CDPI_{1-3}$, MGB1, netropsin, and distamycin (FIG. 6). An example of a minor groove binder is $CDPI_3$ (Kutyavin, 1996; Lukhtanov, 1995) having the structure

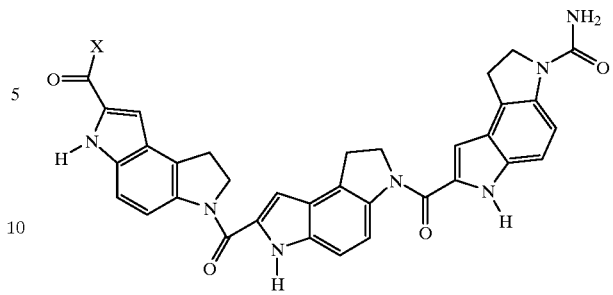

where X is a linker or attachment site for labeling of oligonucleotides. When labelled to oligonucleotides, minor groove binders may increase the affinity and specificity of hybridization to some or substantially most target sequences (Blackburn, 1996, p.337–46).

VII. Nucleic Acid Analogs

Oligonucleotides may contain various nucleic acid analogs bearing modifications to the nucleobase, sugar, and/or internucleotide moieties.

Preferred nucleobase analog modifications include but are not limited to C-5-alkyl pyrimidines, 2-thiopyrimidine, 2,6-diaminopurine, C-5-propyne pyrimidine, phenoxazine (Flanagan, 1999), 7-deazapurine, isocytidine, pseudo-isocytidine, isoguanosine, 4(3 H)-pyrimidone, hypoxanthine, 8-oxopurines and universal base (Meyer, 1994).

Preferred sugar analog modifications in one or more of the nucleosides include but are not limited to 2'- or 3'-modifications where the 2'- or $3^1$-position may be hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo.

Other preferred sugar analog modifications include 4'-α-anomeric nucleotides, 1'-α-anomeric nucleotides, 2'-branching group-ribonucleotides, and 2'-O-branching group-ribonucleotides. The structure below illustrates several preferred 2'-sugar modifications.

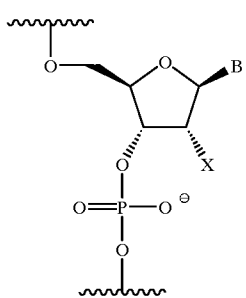

X = $NH_2$, F, Cl, $CH_2CH$=$CH_2$, and OR where R is
$CH_3$, CH=$CHCH_2$, $CH_2CH_2OCH_3$, and lower alkyl Preferred internucleotide analogs between one or more nucleotides include but are not limited to: (i) substitution of oxygen in the internucleotide linkage by sulfur, carbon, or nitrogen, and (ii) sulfate, carboxylate, and amide internucleotide phosphodiester linkages. Other preferred internucleotide analogs include; 2-aminoethylglycine (PNA), 2'-5'-linkage, inverted 3'-3' linkage, inverted 5'-5' linkage, phosphorothioate, phosphorodithioate, methyl phosphonate, non-bridging N-substituted phosphoramidate, alkylated phosphotriester branched structure, and 3'-N-phosphoramidate.

An especially preferred analog of the present invention is the peptide-nucleic acid oligomer, PNA, in which the natural phosphodiester-deoxyribose backbone has been replaced by N-(2-aminoethyl)-glycine, a peptide-like unit (Nielsen, 1991). PNA oligomers are capable of base-pairing with complementary sequences in the clamp-specific portion of the probe by Watson/Crick base-pairing. PNA and PNA/DNA chimera can be synthesized using conventional methods on commercially available, automated synthesizers, with commercially available reagents (Dueholm, 1994; Vinayak, 1997; Van der Laan, 1997).

VIII. Cleaving and Deprotecting Labelled Oligos from Supports

After synthesis, the oligonucleotide may be left on the solid-support, or it may be removed or separated from the solid-support by a cleavage reaction. It is desirable to leave the oligonucleotide on the solid-support because some nucleic acid hybridization assays employ oligonucleotides covalently bound to a solid-support in configurations such as non-porous surfaces, planar-surface arrays, enclosed or encapsulated particles, or loose particles suspended in aqueous media.

Oligonucleotides may be cleaved from the support using a base, e.g., ammonium hydroxide, tert-butyl amine, methylamine, ethylamine, potassium carbonate, or sodium hydroxide. A preferred solution for cleavage and deprotection is a mixture of methanol: tert-butyl amine:water (1:1:2, v:v:v) (Woo, 1993). The cleavage solution also removes phosphate protecting groups, e.g., cyanoethyl, and protecting groups on the exocyclic amines of the nucleobases upon heating the oligonucleotide-containing solution at an elevated temperature, e.g., 55–85° C. for a period of 1 to 16 hours.

Another preferred cleavage method is reductive or oxidative cleavage of a disulfide linker A where A is

where n is 1 to 12. A preferred cleavage reagent is dithiothreitol (DTT).

Another preferred cleavage method is fluoride ion cleavage of a silyl ether linkage A where A is

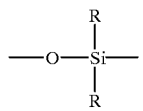

and where R is lower alkyl of 1 to 20 carbon atoms. Preferred cleaving reagents include tetrabutyl ammonium fluoride and hydrogen fluoride/triethylamine.

IX. EXAMPLES

The invention will be further clarified by a consideration of the following examples, which are intended to be purely exemplary of the present invention and not to in any way limit its scope.

EXAMPLE 1

Synthesis of Polystyrene Support-Linker-TAMRA 6

A solution of diglycolic anhydride (64 mg, 0.55 mmol) in $CH_2Cl_2$ (5 ml) was added to a mixture of $Et_3N$ (67 mg, 0.66 mmol), 4-dimethylaminopyridine (34 mg, 0.28 mmol) and compound 1 (400 mg, 0.55 mmol) in $CH_2Cl_2$ (15 ml) at 0° C. under argon atmosphere (FIG. 2). After the addition was complete (10 min), the ice bath was removed and the reaction mixture was stirred at room temperature for 1 h. The reaction mixture was diluted with $CH_2Cl_2$ (30 ml) and washed with 5% aqueous citric acid (1×50 ml) and saturated brine (2×50 ml). The organic layer was dried ($MgSO_4$) and evaporated to give a foam. The product was purified by column chromatography on silica gel eluting with a $CHCl_3$-EtOH gradient (2–10% EtOH). Appropriate fractions were combined and evaporated to give compound 2 as a colorless foam (260 mg, 56%). $^1$H NMR (CDCl3) d: 1.20 (m, 2H), 1.39 (m, 2H), 1.58 (m, 2H), 2.18 (t, J=7.5 Hz, 2H), 2.90–3.25 (m, 4H), 3.80 (s, 6H), 3.86 (s, 4H), 4.00–4.40 (m, 6H), 4.85 (unresolved t, 1H), 5.92 (d, J=7.2 Hz, 1H), 6.75 (d, J=8.1 Hz, 4H), 7.20–7.40 (m, 13H), 7.52 (d, J=7.2 Hz, 2H), 7.69 (d, J=7.2 Hz, 2H).

Highly cross-linked polystyrene 3 (1000Å, 10 µmol/g amine loading, 1 g, 10 µmol), was treated with compound 2 (17 mg, 20 µmol), HOBt (3 mg, 20 µmol), HBTU (8 mg, 20 µmol), and diisopropylethylamine (8 mg, 60 µmol) in DMF (10 ml) on a wrist-action shaker for 4 h at room temperature to give 4. The support was washed with DMF (3×10 ml), $CH_3CN$ (2×10 ml) and $CH_2Cl_2$ (1×10 ml) and dried under high vacuum overnight. A ninhydrin assay showed 0.5 µmol/g amine left on the support. The support was capped with acetic anhydride/lutidine in THF (10% solution, 5 ml) and 1-methylimidazole in THF (16% solution, 5 mL) for 2 h at room temperature. Support 4 was washed with $CH_3CN$ (3×10 ml) and $CH_2Cl_2$ (1×10 ml). Trityl cation assay gave 9.2 µmol/g loading of compound 2 on the polystyrene support. Support 4 was treated with 20% piperidine in DMF (3×10 ml, 10 min each wash) to remove the Fmoc protecting group to give support 5, which was washed with DMF (3×10 ml), $CH_3CN$ (2×10 ml) and $CH_2Cl_2$ (1×10 ml) and, dried under vacuum overnight. Support 5 (1 g, 9.2 µmol) was treated with TAMRA-NHS ester (15 mg, 28.5 µmol) and $Et_3N$ (8.6 mg, 85 µmol) in DMF (10 mL) at room temperature for 36 h on a shaker to give support 6 (L=TAMRA). The support was washed with DMF (3×10 ml), $CH_3CN$ (2 ×10 ml) and $CH_2Cl_2$ (1×10 ml) and dried under high vacuum for 24 h. Ninhydrin test indicated less than 0.5 µmol/g amine left on the support. The support was capped with acetic anhydride/lutidine in THF (10% solution, 5 ml) and 1-methylimidazole in THF (16% solution, 5 ml) for 1 h and then washed with $CH_3CN$ (3×10 ml), $CH_2Cl_2$ (2×10 ml) and dried under high vacuum for 24 h. The trityl cation assay showed a final loading of 8.8 µmol/g for polystyrene support-linker-TAMRA 6.

EXAMPLE 2

Synthesis of FAM-M13-21 Primer on Labelled-Support 6

Synthesis of the FAM-M13-21 primer:

5' FAM-TGTAAAACGACGGCCAGT 3'    SEQ. ID. NO. 1 was conducted on the ABI 394 DNA/RNA synthesizer (Perkin-Elmer Co.) at 0.2 µmole scale with FAM-labelled, polystyrene support 6, (FIG. 2, L=6-carboxyfluorescein FAM, S=polystyrene) The standard 0.2 µmol CE cycle was modified by increasing the coupling time from 25 s to 90 s for coupling of all 5'-phosphoramidite, 3'-DMT phosphoramidite nucleosides 7 (Glen Research). After synthesis in the 5' to 3' direction was complete, FAM-M13-21 primer was cleaved and deprotected in MeOH:t-BuNH$_2$:H$_2$O (1:1:2) at 65° C. for 3 h. The primer was analyzed by conventional means, i.e. anion-exchange HPLC and used in DNA sequencing.

EXAMPLE 3

Labelling of amino-207av 18mer oligonucleotide on Solid-Support with TAMRA-CO$_2$H Synthesis of 5' TCACAGTCTGATCTCGAT 3' was conducted on the ABI 394 DNA/RNA synthesizer (Perkin-Elmer Co.) at 0.2 µmole scale with unlabelled polystyrene support in the 3' to 5' direction with 5'-DMT, 3'-phosphoramidite nucleosides ($A^{bz}$, $G^{dmf}$, $C^{bz}$, T). The amino-linker phosphoramidite reagent 8 (Glen Research) was coupled as the final monomer and detritylated with 3% trichloroacetic acid in CH$_2$Cl$_2$. The synthesis column, bearing the 5'-amino-207av oligonucleotide, was removed from the synthesizer. Two luer-tipped 1 ml syringes were mounted on each end of the synthesis column. One syringe was filled with 10.7 mg (25 µmole) of TAMRA-CO$_2$H in 500 µl dry dimethylformamide (DMF). The second syringe was filled with 9.25 mg (25 µmole) HBTU and 9 µl (50 µmole) diisopropylethylamine in 250 µl of 1:1, DMF:CH$_3$CN. The coupling reagents in the syringes were passed through the column by sequentially depressing each plunger. After thorough mixing for about one minute, the assembly was left to stand for about 15 minutes for the coupling reaction to proceed. The reagents were withdrawn into one syringe and discarded. The synthesis column was washed with 5 ml 1:1, DMF:CH$_3$CN, 5 ml CH$_3$CN, and treated with 1 ml MeOH:t-BuNH$_2$:H$_2$O (1:1:2) to cleave TAMRA-N-207av:

5'TAMRA-N-TCACAGTCTGATCTCGAT 3'    SEQ. ID. NO. 2 from the support. The supernatant containing TAMRA-N-207av was heated and deprotected at 65° C. for 3 h to remove all protecting groups. TAMRA-N-207av was analyzed by reverse-phase HPLC and MALDI-TOF mass spectroscopy which confirmed homogeneous purity and identity.

EXAMPLE 4

Labelling of thiol-oligonucleotide with CDPI3-CO$_2$H

Synthesis of 5' TCACAGTCTGATCTCGAT 3' is conducted on the ABI 394 DNA/RNA synthesizer (Perkin-Elmer Co.) at 0.2 µmole scale with unlabelled polystyrene support in the 3' to 5' direction with 5'-DMT, 3'-phosphoramidite nucleosides ($A^{bz}$, $G^{mf}$, $C^{bz}$, T). The thiol-linker phosphoramidite reagent 10 is coupled as the final monomer and detritylated with silver nitrate in DMF. The synthesis column, bearing the 5'-thiol-207av oligonucleotide, is removed from the synthesizer. Two luer-tipped 1 ml syringes are mounted on each end of the synthesis column. One syringe is filled with 15 mg (25 µmole) of CDPI$_3$-CO$_2$H (FIG. 6, CDPI$_3$, X=OH) in 500 µl dry dimethylformamide (DMF). The second syringe is filled with 9.25 mg (25 µmole) HATU and 9 µl (50 µmole) diisopropylethylamine in 250 µl of 1:1, DMF:CH$_3$CN. The coupling reagents in the syringes are passed through the column by sequentially depressing each plunger. After thorough mixing for about one minute, the assembly is left to stand for about 15 minutes for the coupling reaction to proceed. The reagents are withdrawn into one syringe and discarded. The synthesis column is washed with 5 ml 1:1, DMF:CH$_3$CN, 5 ml CH$_3$CN, and treated with 1 ml MeOH:t-BuNH$_2$:H$_2$O (1:1:2) to cleave CDPI$_3$-S-207av:

5° CDPI$_3$-S-TCACAGTCTGATCTCGAT 3'    SEQ. ID. NO. 3 from the support. The supernatant containing CDPI$_3$-207av is heated and deprotected at 65° C. for 3 h to remove all protecting groups. CDPI$_3$-S-207av is analyzed by reverse-phase HPLC to confirm homogeneous purity. Analysis by MALDI-TOF mass spectroscopy confirms identity.

EXAMPLE 5

Labelling of 5' amino-SG1 Oligonucleotide on Solid-support with NTB-CO$_2$H

Synthesis of 5' ATGCCCTCCCCCATGCCATCCTGCGT 3' was conducted on the ABI 394 DNA/RNA synthesizer (Perkin-Elmer Co.) at 0.2 µmole scale with unlabelled polystyrene support in the 3' to 5' direction with 5'-DMT, 3'-phosphoramidite nucleosides ($A^{bz}$, $G^{dmf}$, $C^{bz}$, T). The amino-linker phosphoramidite reagent 8 (Glen Research) was coupled as the final monomer and detritylated with 3% trichloroacetic acid in CH$_2$Cl$_2$. The synthesis column, bearing the 5'-amino-SG1 oligonucleotide, was removed from the synthesizer. Two luer-tipped 1 ml syringes were mounted on each end of the synthesis column. One syringe was filled with 11 mg (25 µmole) of NTB-CO$_2$H in 500 µl dry dimethylformamide (DMF). The second syringe was filled with 9.25 mg (25 µmole) HBTU and 9 µl (50 µmole) diisopropylethylamine in 250 µl of 1:1, DMF:CH$_3$CN. The coupling reagents in the syringes were passed through the column by sequentially depressing each plunger. After thorough mixing for about one minute, the assembly was left to stand for about 15 minutes for the coupling reaction to proceed. The reagents were withdrawn into one syringe and discarded. The synthesis column was washed with 5 ml 1:1, DMF:CH$_3$CN, 5 ml CH$_3$CN, and treated with 1 ml MeOH:t-BuNH$_2$:H$_2$O (1:1:2) to cleave NTB-N-SG1:

5'NTB-N-ATGCCCTCCCCCATGCCATCCTGCG
T 3'    SEQ. ID. NO. 4 from the support. The supernatant containing NTB-SG1 was heated and deprotected at 65° C. for 3 h to remove all protecting groups. NTB-SG1 was analyzed by reverse-phase HPLC to confirm homogeneous purity. MALDI-TOF mass spectroscopy gave molecular mass of 8390.27 which confirmed identity.

EXAMPLE 6

Labelling of SG1 on Solid-support with NTB-phosphate and MSNT

Synthesis of 5' ATGCCCTCCCCCATGCCATCCTGCGT 3' was conducted on the ABI 384 DNA/RNA synthesizer (Perkin-Elmer Co.) at 0.2 µmole scale with unlabelled polystyrene support in the 3' to 5' direction with 5'-DMT, 3'-phosphoramidite nucleosides ($A^{bz}$, $G^{dmf}$, $C^{bz}$, T). The 5' terminus hydroxyl group was detritylated with 3% trichloroacetic acid in CH$_2$Cl$_2$. The synthesis column, bearing the 5'-hydroxyl-SG1 oligonucleotide, was removed from the synthesizer. Two luer-tipped 1 ml syringes were mounted on each end of the synthesis column. One syringe was filled with 12 mg (25 µmole) of NTB-phosphate in 500 µl dry DMF. The second syringe was filled with 7.5 mg (25µmole) MSNT and 9 µl (50 µmole) diisopropylethylamine in 250 µl DMF. The coupling reagents in the syringes were passed through the column by sequentially depressing each plunger. After thorough mixing for about one minute, the assembly is left to stand for about 60 minutes for the coupling reaction to proceed. The reagents were withdrawn into one syringe and discarded. The synthesis column is washed with 5 ml 1:1, DMF:CH$_3$CN, 5 ml CH$_3$CN, and treated with 1 ml MeOH:t-BuNH$_2$:H$_2$O (1:1:2) to cleave NTB-P-SG1:

5'NTB-P-ATGCCCTCCCCCATGCCATCCTG
    CGT 3'    SEQ. ID. NO. 5 from the support. The supernatant containing NTB-P-SG1 is heated and deprotected at 65° C. for 3 h to remove all protecting groups. NTB-P-SG1 is analyzed by reverse-phase HPLC and MALDI-TOF mass spectroscopy to confirm homogeneous purity and identity.

EXAMPLE 7

Labelling of PNA on Solid-support with MGB1

Automated synthesis of PNA and PNA/DNA chimera was performed using an ABI Model 394 DNA/RNA synthesizer or 433A peptide synthesizer (Perkin-Elmer Co.) according to the general procedures described in the synthesizer manufacturer's Users Manual, as well as Egholm, 1993.

PNA were synthesized at 2–5 μmole scale on MBHA (methylbenzhydrylamine) linker, high-loaded polystyrene support, and with standard synthesis techniques and nucleobase (A$^{bz}$, C$^{bz}$, G$^{ibu}$, T) and primary amino (MMT, Fmoc or Boc) protecting groups, essentially as previously reported (Dueholm, 1994). A 3 ml reaction vessel is used at the 5 μmole scale with a total reaction volume of 440 μl.

PNA were prepared with a carboxy-terminal lysine on MBHA solid support, by preloading with t-Boc-lys(Fmoc). PNA with carboxy-terminal amides were synthesized either directly on an MBHA support or on a MBHA support pre-loaded with the t-Boc T PNA monomer. All resins were loaded to 0.1 to 0.25 mmole/g. A spacer O, 2-(2-aminoethoxy) acetic acid, can be coupled as the Fmoc-amino protected synthon. One or more spacer O units act as a flexible, non-base pairing, hinge region in PNA sequences.

The support used for PNA/DNA chimera synthesis is a non-swelling, high-cross linked polystyrene bead with a hydroxymethylbenzoic acid linker (Vinayak, 1997). PNA monomers for chimera synthesis use the MMT group for primary amino protection. In the first step, the monomer, HATU and DIPEA, each dissolved in DMF/CH$_3$CN, 1/1, are delivered concurrently to the reaction cartridge. After 16 min, capping reagents are delivered. To minimize the tendency of the primary amino function of PNA to migrate or cyclize, the amino terminus is acetylated after removal of the final MMT group. Reagents have been described to link DNA and PNA moieties, and other procedures for chimera synthesis, cleavage, deprotection, and purification (Van der Laan, 1997). In this approach, the chimera can be made continuously in a single cartridge and on a single synthesizer.

PNA oligomer H$_2$N-TCCTCCTT (1 μmole) on solid-support was synthesized by the above procedures. The PNA on polystyrene support was reacted with a mixture of MGB1-CO$_2$H (5 mg, 10 μmole, FIG. 6, Gong, 1997), HATU (10 μmole), 5 μl DIEA and 100 μl DMF and allowed to stand for 1 hour at room temperature. The support was then washed with DMF and CH$_2$Cl$_2$, cleaved with TFMSA (trifluoromethanesulfonic acid) at room temperature for 1 hour, and precipitated in ether to give MGB 1-PNA:

MGB1-TCCTCCTT    SEQ. ID. NO. 6

MGB1-PNA was analyzed by reverse-phase HPLC and MALDI-TOF mass spectroscopy which confirmed homogeneous purity and identity.

EXAMPLE 8

Labelling of PNA on solid-support with CDPI$_3$

By the same procedures and reagents as Example 9, CDPI$_3$ was attached to the PNA H$_2$N-TCCTCCTT by three consecutive couplings of Fmoc-CDPI (FIG. 6, Lukhtanov, 1995) to give CDPI$_3$-labelled PNA. The CDPI monomer unit, 1,2-dihydro-(3H)pyrrolo[3,2-e]indole-7-carboxylate, protected with Fmoc (5 mg, 0.012 mmole) was dissolved in 100 μl NMP and activated by 0.95 equivalents HATU (0.2M in DMF) and 2 equivalents DIEA (0.4 m in DMF). After one hour at room temperature, the activated Fmoc-CDPI solution was added to the support bound PNA and allowed to couple for another hour at room temperature. The support was washed following the coupling with 20 ml DMF. The Fmoc was removed by treatment of the resin support with 1:4 piperidine:DMF for 10 minutes at room temperature. This coupling and deprotection cycle was repeated two additional times for a total of 3 manual couplings. The support was then washed with DMF and CH$_2$Cl$_2$, followed by cleavage with TFMSA (trifluoromethanesulfonic acid) at room temperature for 1 hour, followed by ether precipitation of the crude CDPI$_3$-PNA:

CDPI$_3$-TCCTCCTT    SEQ. ID. NO. 7

CDPI$_3$-PNA was analyzed by reverse-phase HPLC and MALDI-TOF mass spectroscopy which confirmed homogeneous purity and identity

EXAMPLE 9

Labelling of Taqman self-quenching probe on labelled-support 6

The oligonucleotide 5'FAM-CCTGCAGGCCCGTGCCCGT 3' is synthesized on the ABI 384 DNA/RNA synthesizer at 0.2 μmole scale with FAM-labelled, polystyrene support 6, (FIG. 2, L=6-carboxyfluorescein FAM, S=polystyrene) The standard 0.2 μmol CE cycle is modified by increasing the coupling time from 25 s to 90 s for coupling of all 5' phosphoramidite, 3'-DMT phosphoramidite nucleosides (Glen Research). After synthesis in the 5' to 3' direction is complete, the amino-linker phosphoramidite reagent 8 (Glen Research) is coupled as the final monomer at the 3' terminus and detritylated with 3% trichloroacetic acid in CH$_2$Cl$_2$. The synthesis column, bearing the 3'-amino, 5'-FAM oligonucleotide on solid-support, is removed from the synthesizer. Two luer-tipped 1 ml syringes are mounted on each end of the synthesis column. One syringe is filled with 10.7 mg (25 μmole) of TAMRA-CO$_2$H in 500 μl dry dimethylformamide (DMF). The second syringe is filled with 9.25 mg (25 μmole) HBTU and 9 μl (50 μmole) diisopropylethylamine in 250 μl of 1:1, DMF:CH$_3$CN. The coupling reagents in the syringes are passed through the column by sequentially depressing each plunger. After thorough mixing for about one minute, the assembly is left to stand for about 15 minutes for the coupling reaction to proceed. The reagents are withdrawn into one syringe and discarded. The synthesis column is washed with 5 ml 1:1, DMF:CH$_3$CN, 5 ml CH$_3$CN, and treated with 1 ml MeOH:t-BuNH$_2$:H$_2$O (1:1:2) to cleave 5'-FAM, 3'-N-TAMRA Taqman self-quenching probe:

5'FAM-CCTGCAGGCCCGTGCCCGT-N-
    TAMRA 3'    SEQ. D. NO. 8 from the support. The supernatant containing the probe is heated and deprotected at 65° C. for 3 h to remove all protecting groups. The probe is analyzed by reverse-phase HPLC and MALDI-TOF mass spectroscopy which confirmed homogeneous purity and identity.

All publications and patent applications are herein incorporated by reference to the same extent as if each individual publication or patent application was specifically and individually indicated to be incorporated by reference.

Although only a few embodiments have been described in detail above, those having ordinary skill in the molecular biology and chemistry arts will clearly understand that many modifications are possible in the preferred embodiment without departing from the teachings thereof. All such modifications are intended to be encompassed within the following claims.

We claim:

1. A method for 5' to 3' synthesis of 5' labelled oligonucleotides comprising the steps of:
   a) providing a labelled solid-support having the structure

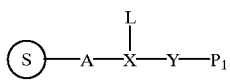

where,
   S is a solid-support;
   A is a cleavable linker;
   X is a moiety with three or more attachment sites;
   L is a label;
   Y is selected from the group consisting of oxygen, NH, NR where R is methyl, lower alkyl, substituted alkyl, phenyl, aryl, and substituted aryl, and sulfur; and
   $P_1$ is an acid-cleavable protecting group;
   b) reacting the labelled solid-support with acid to remove the acid-cleavable protecting group, $P_1$; and
   c) adding a 5'-phosphoramidite, 3' protected nucleoside and an activator, thereby forming a bond between Y 5' terminus of the and the nucleoside.

2. The method of claim 1 further comprising the steps of
   d) capping any unreacted sites on the solid-support; and
   e) adding an oxidizing reagent.

3. The method of claim 1 further comprising the steps of
   d) capping any unreacted sites on the solid-support;
   e) adding an oxidizing reagent; and
   f) repeating steps (b) to (c) until the labelled oligonucleotide is completely synthesized.

4. The method of claim 3 further comprising the step of deprotecting the labelled oligonucleotide.

5. The method of claim 3 further comprising the steps of cleaving the labelled compound from the solid-support and deprotecting the labelled oligonucleotide.

6. The method of claim 1 wherein the solid-support S is selected from the group consisting of polystyrene, controlled-pore-glass, silica gel, silica, polyacrylamide, magnetic beads, polyacrylate, hydroxyethylmethacrylate, polyamide, polyethylene, polyethyleneoxy, and copolymers and grafts of such.

7. The method of claim 1 wherein the form of the solid support S is selected from the group consisting of small particles, beads, membranes, frits, slides, plates, micromachined chips, alkanethiol-gold layers, non-porous surfaces, addressable arrays, and polynucleotide-immobilizing media.

8. The method of claim 1 wherein the cleavable linker A is selected from the group consisting of:

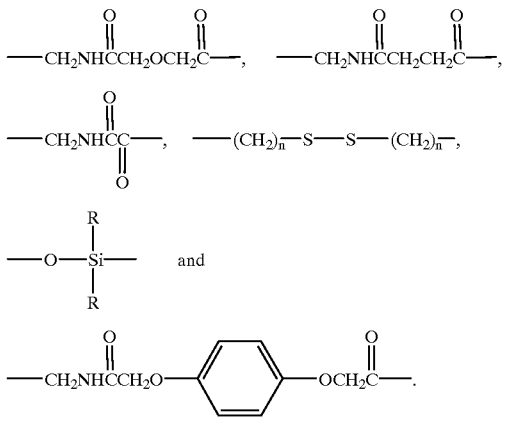

9. The method of claim 1 wherein the linker X is selected from the group consisting of:

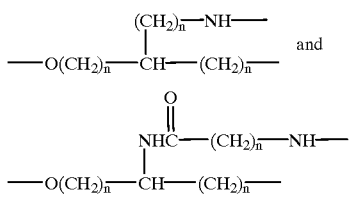

where n is 1 to 12.

10. The method of claim 1 wherein the label L is selected from the group consisting of hybridization-stabilizing moieties, fluorescent dyes, fluorescence quenchers, energy-transfer dye sets, chemiluminescent dyes, amino acids, proteins, peptides, enzymes, and affinity ligands.

11. The method of claim 10 where the fluorescent dyes and fluorescence quenchers are selected from the group consisting of FAM, TET, HEX JOE, TAMRA, d-TAMRA, JODA, ROX, VIC, NED, dJON, dR139, DABCYL, DABSYL, malachite green, 4,7-dichloro-fluoresceins, 4,7-dichloro-rhodamines, NTB, and cyanines.

12. The method of claim 10 where the hybridization-stabilizing moieties are selected from the group consisting of Hoechst 33258, CDPI$_{1-3}$, MGB1, netropsin, and distamycin.

13. The method of claim 1 wherein the acid-cleavable protecting group P$_1$ is selected from the group consisting of DMT, MMT, trityl, substituted trityl, pixyl, and trialkylsilyl.

14. The method of claim 1 wherein the 5'-phosphoramidite, 3' protected nucleoside monomer has the structure:

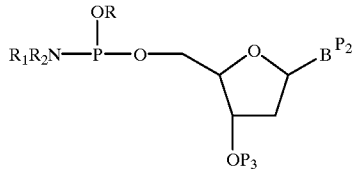

where,

R is selected from the group consisting of cyanoethyl, methyl, lower alkyl, substituted alkyl, phenyl, aryl, and substituted aryl;

R$_1$ and R$_2$ are individually selected from the group consisting of isopropyl, morpholino, methyl, ethyl, lower alkyl, cycloalkyl, and aryl;

P$_2$ is an exocyclic nitrogen protecting group selected from the group consisting of benzoyl, isobutyryl, acetyl, phenoxyacetyl, aryloxyacetyl, dimethylformamidine, dialkylformamidine, and dialkylacetamidine; and P$_3$ is an acid-labile protecting group selected from the group consisting of DMT, MMT, pixyl, trityl, and trialkylsilyl.

15. The method of claim 3 wherein the oligonucleotide comprises one or more DNA, RNA, and nucleic acid analog monomer units wherein the nucleic acid analog is selected from the group consisting of nucleobase analogs, sugar analogs, and internucleotide analogs.

16. The method of claim 15 wherein nucleobase analogs are selected from the group consisting of C-5-alkyl pyrimidine, 2,6-diaminopurine, 2-thiopyrimidine, C-5-propyne pyrimidine, phenoxazine, 7-deazapurine, isocytidine, pseudo-isocytidine, isoguanosine, hypoxanthine, 8-oxopurine, and universal base.

17. The method of claim 15 wherein sugar analogs are selected from the group consisting of 2'-O-alkyl-ribonucleotides, 2'-O-methyl-ribonucleotides, 2'-O-allyl-ribonucleotides, 2'-allyl-ribonucleotides, 2'-halo-ribonucleotides, 2'-O-methoxyethyl-ribonucleotides, 2'-branching group-ribonucleotides, 2'-O-branching group-ribonucleotides, 4'-α-anomeric nucleotides, and 1'-α-anomeric nucleotides.

18. The method of claim 15 wherein internucleotide analogs are selected from the group consisting of 2-aminoethylglycine (PNA), 2'-5'-linkage, inverted 3'-3' linkage, inverted 5'-5' linkage, phosphorothioate, methyl phosphonate, non-bridging N-substituted phosphoramidate, alkylated phosphotriester branched structure, and 3'-N-phosphoramidate.

19. The method of claim 1 wherein the labelled solid-support comprises a compound of the formula

where S is polystyrene or controlled-pore-glass; and

L is a label.

20. A solid-support comprising a compound of the formula

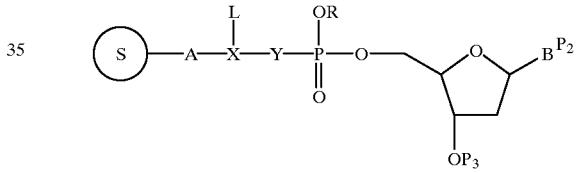

where,

S is a solid-support;

A is a cleavable linker;

X is a moiety with three or more attachment sites;

L is a label;

Y is selected from the group consisting of O, NH, NR, and S;

R is selected from the group consisting of cyanoethyl, methyl, lower alkyl, substituted alkyl, phenyl, aryl, and substituted aryl;

P$_2$ is an exocyclic nitrogen protecting group selected from the group consisting of benzoyl, isobutyryl, acetyl, phenoxyacetyl, aryloxyacetyl, dimethylformamidine, dialkylformamidine, and dialkylacetamidine; and P$_3$ is acid-labile protecting group selected from the group consisting of DMT, MMT, trityl, substituted trityl, pixyl, and trialkylsilyl.

21. A solid-support comprising a compound of the formula

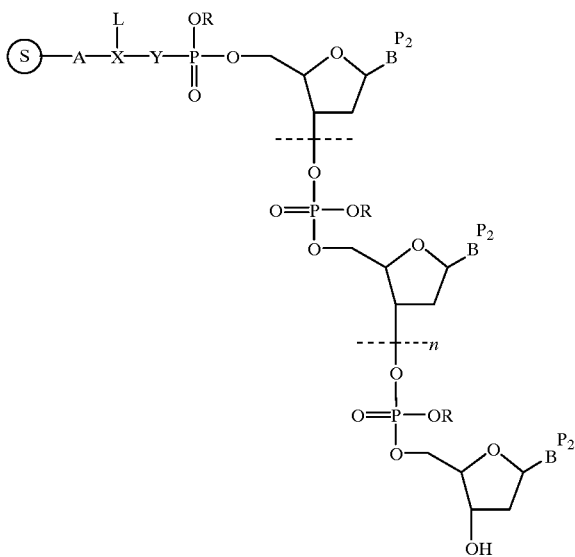

where n is an interger from 0 to 100;
S is a solid-support;
A is a cleavable linker;
X is a moiety with three or more attachment sites;
L is a label;
Y is selected from the group consisting of O, NH, NR, and S;
R is cyanoethyl, methyl, lower alkyl, substituted alkyl, phenyl, aryl, and substituted aryl;
$P_2$ is an exocyclic nitrogen protecting group selected from the group consisting of benzoyl, isobutyryl, acetyl, phenoxyacetyl, aryloxyacetyl, dimethylformamidine, dialkylformamidine, and dialkylacetamidine.

22. A method to synthesize a labelled oligonucleotide comprising:
synthesizing an oligonucleotide on a solid support wherein the oligonucleotide includes nucleophilic functionality consisting of alcohol, amine, or thiol, and
coupling a label reagent with functionality consisting of carboxylic acid, sulfonic acid, phosphonic acid, or phosphoric acid; to the oligonucleotide
bound to the solid support with a coupling reagent;
wherein the coupling reagent is HATU, HBTU, TBTU, BOP, PyBOP, EEDQ, DCC, DIPCDI, HOBt, MSNT, triisopropylbenzenesulfonyl chloride, or an aryl sulfonyl halide;
whereby an ester, amide, thioester, sulfonamide, sulfonate, phosphonate, phosphoramidate, phosphorothioate, or phosphate bond is formed.

23. The method of claim 22 wherein the label reagents are selected from the group consisting of hybridization-stabilizing moieties, fluorescent dyes, fluorescence quenchers, energy-transfer dye sets, chemiluminescent dyes, amino acids, proteins, peptides, enzymes, and affinity ligands.

24. The method of claim 23 where the fluorescent dyes and fluorescence quenchers are selected from the group consisting of FAM, TET, HEX, JOE, TAMPA, d-TAMRA, JODA, ROX, VIC, NED, dJON, dR139, DABCYL, DABSYL, malachite green, 4,7-dichloro-fluoresceins, 4,7-dichloro-rhodamines, NTB, and cyanines.

25. The method of claim 23 where the hybridization-stabilizing moieties are selected from the group consisting of Hoechst 33258, $CDPI_{1-3}$, MGB1, netropsin, and distamycin.

26. The method of claim 22 wherein the labels are attached to the oligonucleotide at label sites consisting of the 5' terminus, the 3' terminus, a nucleobase, an internucleotide linkage, a sugar, amino, sulfide, hydroxyl, and carboxyl.

27. The method of claim 22 wherein the solid-support is selected from the group consisting of polystyrene, controlled-pore-glass, silica gel, silica, polyacrylamide, magnetic beads, polyacrylate, hydroxethylmethacrylate, polyamide, polyethylene, polyethyleneoxy, and copolymers or grafts of such.

28. The method of claim 27 wherein the form of the solid support is selected from the group consisting of small particles, beads, membranes, frits, non-porous surfaces, slides, plates, micromachined chips, alkanethiol-gold layers, addressable arrays, or polynucleotide-immobilizing media.

29. The method of claim 22 wherein the oligonucleotide comprises one or more DNA, RNA, PNA and nucleic acid analog monomer units wherein the nucleic acid analog is selected from the group consisting of nucleobase analogs, sugar analogs, and internucleotide analogs.

30. The method of claim 29 wherein nucleobase analogs are selected from the group consisting of C-5-alkyl pyrimidine, 2,6-diaminopurine, 2-thiopyrimidine, C-5-propyne pyrimidine, phenoxazine, 7-deazapurine, isocytidine, pseudo-isocytidine, isoguanosine, hypoxanthine, 8-oxopurine, and universal base.

31. The method of claim 29 wherein sugar analogs are selected from the group consisting of 2'-O-alkyl-ribonucleotides, 2'-O-methyl-ribonucleotides, 2'-O-allyl-ribonucleotides, 2'-allyl ribonucleotides, 2'-halo-ribonucleotides, 2'-O-methoxyethyl-ribonucleotides, 2'-branching group-ribonucleotides, 2'-O-branching group-ribonucleotides, 4'-α-anomeric nucleotides, and 1'-α-anomeric nucleotides.

32. The method of claim 29 wherein internucleotide analogs are selected from the group consisting of 2-aminoethylglycine (PNA), 2'-5'-linkage, inverted 3'-3' linkage, inverted 5'-5' linkage, phosphorothioate, methyl phosphonate, non-bridging N-substituted phosphoramidate, alkylated phosphotriester branched structure, and 3'-N-phosphoramidate.

33. The method of claim 22, wherein the direction of oligonucleotide synthesis is 5' to 3'.

34. The method of claim 22, wherein the direction of oligonucleotide synthesis is 3' to 5'.

* * * * *